United States Patent
Leedom et al.

(10) Patent No.: US 7,987,977 B2
(45) Date of Patent: *Aug. 2, 2011

(54) HEARING AID PACKAGE

(75) Inventors: Marvin A. Leedom, Princeton, NJ (US);
John G. Aceti, Cranbury, NJ (US);
Walter P. Sjursen, Washington Crossing, PA (US); Derek D. Mahoney, Manalapan, NJ (US); John M. Margicin, Levittiown, PA (US); Michael H. Tardugno, Lawrenceville, NJ (US); Robert R. Demers, Cranbury, NJ (US); John E. Oltman, Mt. Horeb, WI (US); Robert C. Maxwell, Princeton, NJ (US); Frederick J. Fritz, Skillman, NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/880,864

(22) Filed: Jun. 30, 2004

(65) Prior Publication Data

US 2004/0240695 A1    Dec. 2, 2004

Related U.S. Application Data

(63) Continuation of application No. 09/524,501, filed on Mar. 13, 2000, now Pat. No. 7,010,137, which is a continuation-in-part of application No. 09/263,593, filed on Mar. 5, 1999, now Pat. No. 6,473,511, which is a continuation-in-part of application No. 08/815,852, filed on Mar. 12, 1997, now Pat. No. 5,881,159.

(60) Provisional application No. 60/157,972, filed on Oct. 6, 1999, provisional application No. 60/157,870, filed on Oct. 6, 1999, provisional application No. 60/145,321, filed on Jul. 23, 1999, provisional application No. 60/161,214, filed on Oct. 22, 1999, provisional application No. 60/013,426, filed on Mar. 14, 1996.

(51) Int. Cl.
*B65D 85/00* (2006.01)
*B65D 81/24* (2006.01)
*H04R 25/00* (2006.01)

(52) U.S. Cl. .................... 206/305; 206/213.1; 381/312; 381/322

(58) Field of Classification Search .................. 206/205, 206/210, 213.1, 204, 524.1, 524.4, 524.6, 206/525, 305, 363, 320, 349, 438, 523, 524, 206/484–484.2, 524.8, 701–728; 381/312–331; 181/126, 130, 135; 588/877; 428/35.3, 35.7
See application file for complete search history.

(56) References Cited

U.S. PATENT DOCUMENTS 3,312,789 A * 4/1967 Lewis et al. .................. 381/323
(Continued)

FOREIGN PATENT DOCUMENTS

DE    3406972 A1    8/1985
(Continued)

OTHER PUBLICATIONS

"A Breakthrough in Hearing Technology",—*The Philips XP Peritympanic*, Philips.
(Continued)

*Primary Examiner* — Bryon P Gehman
(74) *Attorney, Agent, or Firm* — Hamilton, Brook, Smith & Reynolds, P.C.

(57) ABSTRACT

A hearing aid is enclosed in a gas-impermeable or substantially gas-impermeable package to prevent inadvertent activation of the hearing aid during transport. The package may include a housing having a groove that substantially conforms to at least a portion of the shape of the hearing aid to snugly hold the hearing aid. The groove may be substantially open adjacent a switch on the hearing aid. A securing member, such as a strap, may be used to immobilize the switch relative to the housing.

22 Claims, 17 Drawing Sheets

U.S. PATENT DOCUMENTS

| Patent | Type | Date | Inventor | Ref |
|---|---|---|---|---|
| 3,527,901 | A | 9/1970 | Geib | |
| 3,598,928 | A | 8/1971 | Hickox | |
| 3,625,351 | A * | 12/1971 | Eisenberg | 206/484 |
| 3,783,201 | A | 1/1974 | Weiss | |
| 3,801,011 | A * | 4/1974 | Guehler et al. | 206/205 |
| 3,870,741 | A * | 3/1975 | Kuhn | 206/524 |
| 3,890,474 | A | 6/1975 | Glicksberg | |
| 4,015,708 | A * | 4/1977 | Kelm | 206/704 |
| 4,051,066 | A * | 9/1977 | Miksic et al. | 252/389.5 |
| 4,053,051 | A * | 10/1977 | Brinkhoff | 206/438 |
| 4,068,090 | A | 1/1978 | Komatsu et al. | |
| 4,209,091 | A * | 6/1980 | Lieberman | 206/704 |
| 4,321,998 | A * | 3/1982 | Van de Walker et al. | 206/229 |
| 4,343,869 | A | 8/1982 | Oltman et al. | |
| 4,379,988 | A | 4/1983 | Mattatall | |
| 4,539,440 | A | 9/1985 | Sciarra | |
| 4,591,539 | A | 5/1986 | Oltman et al. | |
| 4,617,242 | A | 10/1986 | Dopp | |
| 4,622,440 | A | 11/1986 | Slavin | |
| 4,639,556 | A | 1/1987 | Hartl et al. | |
| 4,649,034 | A | 3/1987 | Rutledge | |
| 4,711,352 | A * | 12/1987 | Williams et al. | 206/365 |
| 4,712,245 | A | 12/1987 | Lyregaard | |
| 4,716,985 | A * | 1/1988 | Haertl | 181/130 |
| 4,730,726 | A * | 3/1988 | Holzwarth | 206/204 |
| 4,739,512 | A | 4/1988 | Hartl et al. | |
| 4,777,780 | A * | 10/1988 | Holzwarth | 53/432 |
| 4,870,688 | A | 9/1989 | Voroba et al. | |
| 4,937,115 | A * | 6/1990 | Leatherman | 428/36.4 |
| 4,969,534 | A | 11/1990 | Kolpe et al. | |
| 4,999,265 | A | 3/1991 | Dopp | |
| 5,002,151 | A | 3/1991 | Oliveira et al. | |
| 5,012,520 | A | 4/1991 | Steeger | |
| 5,141,455 | A | 8/1992 | Ponn | |
| 5,146,051 | A | 9/1992 | Hermann | |
| 5,160,700 | A * | 11/1992 | Anderson et al. | 422/34 |
| 5,185,802 | A * | 2/1993 | Stanton | 381/328 |
| 5,203,455 | A * | 4/1993 | Hewelt et al. | 206/704 |
| 5,234,105 | A * | 8/1993 | Sato et al. | 206/706 |
| 5,234,106 | A * | 8/1993 | Transue et al. | 206/363 |
| 5,253,300 | A | 10/1993 | Knapp | |
| 5,254,414 | A | 10/1993 | Tsenter | |
| 5,286,407 | A * | 2/1994 | Inoue et al. | 206/204 |
| 5,308,711 | A | 5/1994 | Passaniti et al. | |
| 5,347,584 | A | 9/1994 | Narisawa | |
| 5,357,576 | A | 10/1994 | Arndt | |
| 5,364,045 | A * | 11/1994 | Clayton et al. | 206/213.1 |
| 5,378,562 | A | 1/1995 | Passaniti et al. | |
| 5,449,569 | A * | 9/1995 | Schumm, Jr. | 429/27 |
| 5,510,209 | A | 4/1996 | Abraham et al. | |
| 5,640,783 | A * | 6/1997 | Schumaier | 34/219 |
| 5,669,501 | A * | 9/1997 | Hissong et al. | 206/438 |
| 5,690,226 | A * | 11/1997 | N'Guyen | 206/438 |
| 5,707,499 | A | 1/1998 | Joshi et al. | |
| 5,712,058 | A | 1/1998 | Malay | |
| 5,721,072 | A | 2/1998 | Mototani et al. | |
| 5,724,431 | A | 3/1998 | Reiter et al. | |
| 5,742,007 | A * | 4/1998 | Kornowski et al. | 174/52.3 |
| 5,749,203 | A * | 5/1998 | McGowan, Jr. | 53/432 |
| 5,763,503 | A * | 6/1998 | Cowperthwaite et al. | 522/44 |
| 5,784,860 | A * | 7/1998 | Fujikawa et al. | 206/524.8 |
| 5,825,896 | A | 10/1998 | Leedom | |
| 5,889,874 | A | 3/1999 | Schmitt et al. | |
| 5,949,895 | A | 9/1999 | Ball et al. | |
| 6,041,128 | A | 3/2000 | Narisawa et al. | |
| 6,041,129 | A | 3/2000 | Adelman | |
| 6,097,825 | A | 8/2000 | Yoest et al. | |
| 6,143,440 | A | 11/2000 | Volz et al. | |
| 6,161,695 | A * | 12/2000 | Nicolais | 206/438 |
| 6,170,663 | B1 * | 1/2001 | Glassman | 206/461 |
| 6,208,741 | B1 | 3/2001 | Shennib et al. | |
| 6,212,283 | B1 | 4/2001 | Fletcher et al. | |
| 6,253,871 | B1 * | 7/2001 | Aceti | 381/328 |
| 6,257,402 | B1 * | 7/2001 | Hedman | 206/204 |
| 6,283,915 | B1 * | 9/2001 | Aceti et al. | 600/300 |
| 6,410,997 | B1 * | 6/2002 | Sjursen et al. | 307/130 |
| 6,473,511 | B1 | 10/2002 | Aceti et al. | |
| 6,473,513 | B1 | 10/2002 | Shennib et al. | |
| 6,546,108 | B1 | 4/2003 | Shennib et al. | |
| 6,567,527 | B1 | 5/2003 | Baker et al. | |
| 6,724,902 | B1 | 4/2004 | Shennib et al. | |
| 6,751,327 | B1 | 6/2004 | Urso et al. | |
| 2002/0085728 | A1 | 7/2002 | Shennib et al. | |

FOREIGN PATENT DOCUMENTS

| | | | |
|---|---|---|---|
| EP | 0259574 | * | 3/1988 |
| GB | 1468120 | | 3/1977 |
| JP | 62-176185 | | 8/1987 |
| JP | 4-113800 | | 4/1992 |
| JP | 4-199999 | | 7/1992 |
| JP | 4-269100 | | 9/1992 |
| WO | WO 93/25053 | | 12/1993 |
| WO | WO 97/04619 | | 2/1997 |
| WO | WO 97/34443 | | 9/1997 |

OTHER PUBLICATIONS

"The Invisible Pathway to Natural Hearing",—*The Joy of Better Hearing*, Philips.

Voroba, B., "Patient-Selected Soft Canal Hearing Instruments," *Hearing Instruments*, 38(4) (1987).

* cited by examiner

HEARING AID PACKAGE

RELATED APPLICATIONS

This application is a continuation of U.S. application Ser. No. 09/524,501 filed Mar. 13, 2000, now U.S. Pat. No. 7,010, 137, which is a continuation-in-part of U.S. application Ser. No. 09/263,593 filed Mar. 5, 1999, now U.S. Pat. No. 6,473, 511, which is a continuation-in-part of U.S. application Ser. No. 08/815,852 filed Mar. 12, 1997, now U.S. Pat. No. 5,881, 159, the entire teachings of each application being incorporated herein by reference. This application also claims benefit to Application Ser. Nos. 60/157,972 filed Oct. 6, 1999; 60/157,870 filed Oct. 6, 1999; 60/145,321 filed Jul. 23, 1999; and 60/161,214 filed Oct. 22, 1999, the entire teachings of each being incorporated herein by reference. U.S. application Ser. No. 08/815,852 filed Mar. 12, 1997, now U.S. Pat. No. 5,881,159, claims the benefit of U.S. Provisional Application No. 60/013,426, filed Mar. 14, 1996.

This application is related to U.S. Application Ser. Nos. 09/524,040; 09/524,043; 60/188,721; 60/188,857, 60/188, 996; 60/188,997; entitled "Disposable Modular Hearing Aid", all filed on Mar. 13, 2000, the entire teachings of each application being incorporated herein by reference.

BACKGROUND OF THE INVENTION

Modern hearing aids comprise an earmold having therein the necessary electronics for amplifying and otherwise conditioning sound to compensate for a user's hearing loss. Such electronics generally include a microphone for receiving the sound and converting the sound to an electrical signal, an electronic circuit for amplifying and processing the signal produced by the microphone, a speaker (also known as a receiver) for converting the processed signals into sound energy and a battery for providing operational power to the hearing aid. The earmold can be generally made of plastic, and is specially designed and molded to fill the ear of the person who is to use the hearing aid. Generally, the earmold is made of a hard plastic so as to have a long life and so that it can be periodically cleaned. The electronics of the signal processing circuitry are typically adjusted to meet its users specific hearing requirements. These requirements are obtained by first testing the user's hearing and then providing a circuit having a frequency response characteristic that compensates for any hearing loss discovered in the test. After the desired circuit is determined from the tests, it may be finally adjusted by a hearing aid specialist to meet the final requirements of the party. All of the above features of the structure of the hearing aid, the method of making it and the method of adjusting it make the hearing aid relatively expensive.

Conventionally, hearing aids have a battery that must be replaced periodically as it is small and has only a limited lifetime of operation. Hearing aid users frequently complain about the difficulty in replacing batteries. Batteries are becoming increasingly difficult to handle as hearing aids and batteries become smaller. It is especially difficult for the majority of hearing aid wearers who are over 65 years of age and who are losing visual and motor abilities. Having a hearing aid that does not require battery replacement, or replacement at fewer time intervals, would be advantageous to these users.

SUMMARY OF THE INVENTION

One solution to this problem is to provide a disposable hearing aid with a permanent battery, as is disclosed in U.S. Pat. No. 5,881,159, issued to Aceti et al. on Mar. 9, 1999. One difficulty with a disposable hearing aid, however, is that its permanent battery may discharge during the shelf-life period. To ensure that the hearing aid lasts for its target life of 30 days, for example, a switch may be included in the device to keep the battery from discharging. Two types of switches may be used: an on/off switch or an on-only switch. An on-only switch may be used to activate the device once. Once put into service the device remains "on" until the battery is depleted. An on/off switch, in addition to activating the device once, may allow the hearing aid to be turned "off" during non-use periods, for example at sleep time.

It would also be desirable to have a disposable hearing aid which is inexpensive with regard to both the structure of the parts of the hearing aid and its method of making and packaging, and which can be easily used by the person, particularly the elderly.

The present invention is directed to a hearing aid having an integral power source or battery. The integral power source is for example, non-replaceable or non-removable. The hearing aid includes a circuit for receiving and amplifying the sound, and a shell surrounding the circuit.

In one embodiment, the battery is customized and substantially conforms to a portion of the ear canal between the aperture and the first bend. The battery can be tapered and include at least one step. In one embodiment, the battery has an elliptical cross-section. The battery may have a metal or plastic enclosure. The battery can be used in a disposable or non-disposable hearing aid.

The present invention is also directed to a hearing aid insertable into an ear canal which includes a microphone which translates acoustic energy into electrical signals, signal processing circuitry which processes the electrical signals provided by the microphone, a receiver which converts the processed electrical signals into acoustic energy, and a power source connectable to the signal processing circuitry. Preferably, the power source substantially conforms to a portion of the ear canal between the aperture and the first bend. The hearing aid can further include a housing formed of two half-shells jointed together and enclosing one or more of the microphone, the signal processing circuitry, and the receiver.

In another embodiment, the power source is disposed between the microphone and the receiver to prevent feedback between the same. A flexible circuit preferably interconnects the power source and receiver.

A battery is also provided in accordance with the present invention for a hearing aid which includes a plastic housing partially surrounding a metal shell. The metal shell is expandable and contains zinc and electrolyte. A plastic cathode plate seals one end of the metal shell and a cathode grid is positioned proximate to the plastic cathode plate. At least one cathode electrode and at least one anode electrode is disposed in the cathode plate.

An apparatus and a method for automatically shutting down or disabling a hearing aid is also provided which includes an apparatus for calculating the total time the hearing aid is turned "on" excluding the time the hearing aid is turned "off." The hearing aid is shut down upon reaching a predetermined amount of total time that the hearing aid is turned "on". Preferably, the user is warned prior to shut down of the hearing aid. The hearing aid can also be shut down by disconnecting a receiver of the hearing aid.

In another embodiment, a continuous amount of time is calculated starting when the hearing aid is turned "on" and the hearing aid is shut down upon reaching a predetermined amount of time.

In yet another embodiment, a method is provided for automatically shutting down a hearing aid which includes programming electronics of the hearing aid such that the hearing aid will operate only during a predetermined time interval. The hearing aid is activated by turning it "on" during the predetermined time interval.

In accordance with other principles of the present invention, the hearing aid can have a generally cylindrical base portion, an elongate curved middle portion, and a mushroom-shaped tip portion. A battery is provided having a stepped shape to conform to the interior of the hearing aid.

In accordance with other aspects, a hearing aid insertable into an ear canal is provided which includes a microphone which translates acoustic energy into electrical signals, signal processing circuitry which processes the electrical signals provided by the microphone, a receiver which converts the processed electrical signals into acoustic energy, and a power source connectable to the signal processing circuitry. A shell encloses the microphone, the signal processing circuitry, and the receiver. Preferably, the shell includes a substantially transparent or translucent faceplate which is externally visible after the hearing aid is inserted into the ear canal. This allows the faceplate to pick up the natural color of the user's ear to help conceal the hearing aid within the ear during use. The faceplate can include a reflective surface thereon and can also include compound curves.

According to further aspects of the present invention, a coupling mechanism is provided that simultaneously electrically connects the signal processing circuitry, the receiver, and the power source. In one embodiment, the coupling mechanism includes contact members such as leaf springs having twisted ends for ensuring an electrical connection.

According to yet further aspects, a switch mechanism is provided that turns the hearing aid "on", i.e., connects the battery (power source) terminals to the circuit, upon insertion of the hearing aid into the ear canal and turns the hearing aid "off" upon removal of the hearing aid from the ear canal. In one embodiment, the switch mechanism includes a pull cord connected to an insulating member. The insulating member breaks a circuit between the power source and the signal processing circuitry to turn the hearing aid "off".

In other aspects, it can be desirable to provide more than one power source to extend the use life of the hearing aid. Accordingly, a hearing aid is provided which includes more than one power source. A switch mechanism is provided for selecting and activating a single power source. In one embodiment, the switch mechanism includes an insulating member which, in an "off" position, covers a hole of each metal/battery power source to prevent air from entering into the power source. The switch mechanism further includes a conducting member for connecting, in an "on" position, the first power source or the second power source to the signal processing circuitry of the hearing aid. Preferably, the switch mechanism further includes an aperture therethrough for allowing an air pathway to allow air to enter the selected power source to activate the same.

In accordance with further aspects of the present invention, packaging is provided for a hearing aid to prevent inadvertent activation of the hearing aid during transport. Preferably, the packaging includes a housing having a groove that substantially conforms to at least a portion of the shape of the hearing aid to snuggly hold the hearing aid. The groove, in one embodiment, is substantially open adjacent the switch. A securing member, such as a strap, can be used to immobilize the switch relative to the housing.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
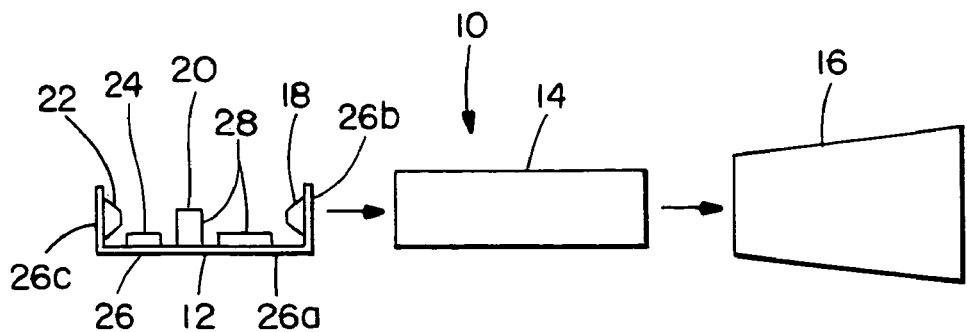
FIG. 1 is an exploded schematic view of a first embodiment of a hearing aid according to the present invention.
Figure 2:
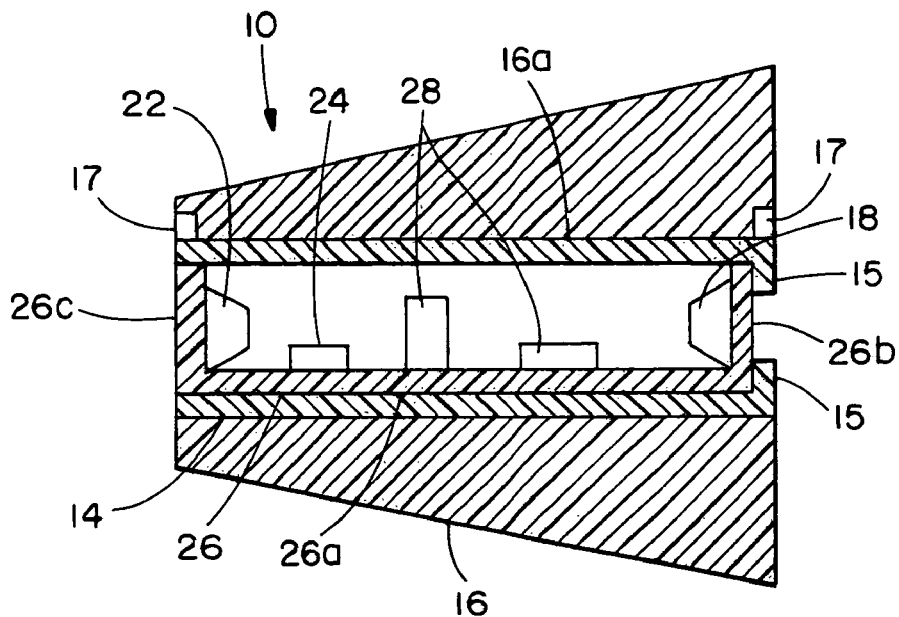
FIG. 2 is a sectional view of the assembled hearing aid shown in FIG. 1.
Figure 3:
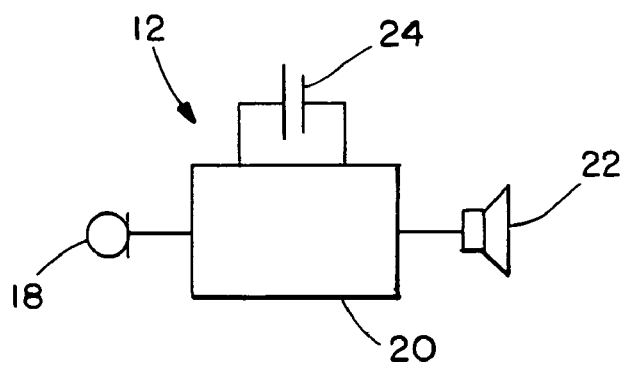
FIG. 3 is a schematic diagram, partly in block diagram form, of the components of a hearing aid according to the present invention.

A description of preferred embodiments of the invention follows. Referring initially to FIGS. 1 and 2 of the drawings, the hearing aid of the present invention is generally designated as 10. Hearing aid 10 comprises an electronics assembly 12, a shell 14 and an earmold 16. As shown in FIG. 3, the electronics assembly 12 includes a microphone 18, which is adapted to receive the sound and convert the sound into electrical signals. The microphone 18 is connected to the input of a signal processing circuitry 20 which amplifies the sound, diminishes any undesirable background noise and which can adjust the sound according to the particular needs of the hearing of the user. The output of the signal processing circuitry is connected to a receiver 22 which converts the output signals to sound and directs the sound into the ear of the user. A suitable battery 24 is connected to the signal processing circuitry 20 to operate the circuitry 20.

As shown in FIGS. 1 and 2, the electronics assembly 12 includes a flexible printed circuit 26 having a base 26a and upright arms 26b and 26c at its ends. The flexible printed circuit 26 also includes therein paths of a conductive metal (not shown). The microphone 18 is mounted on the upright arm 26b at one end of the printed circuit 26, and the receiver 22 is mounted on the upright arm 26c at the other end of the printed circuit 26. The components 28 of the signal processing circuitry 20 and the battery 24 are mounted on the base 26a of the printed circuit 26 between its ends. The microphone 18 can be any very small microphone, which is presently on the market or can be a silicon microphone in which the diaphragm of the microphone 18 is a thin layer of silicon.

The signal processing circuitry 20 can be of any well-known type, which will provide the desired amplification. For a very short operating hearing aid 10, such as for a three-day operation, the signal processing circuitry 20 can be of the type, which will provide amplification with fixed gain and frequency response. A simple, low-cost class-A amplifier can be used. For a longer lasting hearing aid 10, such as a 30-day device, the signal processing circuitry 20 can be of the type, which contains a two-channel amplifier with signal compression. One channel can process the lower frequency spectrum while the other channel can process the higher frequency spectrum. To extend battery life, a more efficient class-D output amplifier can be used. For any type of signal processing circuitry 20, integrated circuits that perform the required signal processing should be used and are readily available. To achieve the different responses, different values of passive components, such as resistors and capacitors, can be used. The speaker 22 can be of any type of small speaker readily available. Various embodiments of the battery or power source 24, which is used to operate the signal processing circuitry 20, will be described below.

The shell 14 can be, for example, a flexible hollow cylindrical element that is adapted to house and protect the electronics assembly 12. The shell 14 can be molded, plastic material and contains means, such as ribs 15 shown in FIG. 2, to orient and retain the electronics assembly 12 therein. The shell 14 is of a material, which protects the electronics assembly 12 from moisture and mechanical damage. The shell 14 also provides acoustical features for facilitating incoming and outgoing sound, and has external features, such as ribs 17, which help retain it in the earmold 16.

In one embodiment, earmold 16 is of a soft, durable and-compliant material. It can be of a cold-cured methacrylate, heat-cured methacrylate, heat-cured silicone, polyvinyl chloride copolymer or polyethylene co-polymer. The earmold 16 has an inner opening 16a into which the shell 14 containing the electronics assembly 12 is inserted and retained. The outer configuration of the earmold 16, such as its shape and size, is such that it can be readily inserted in the ear canal of the user and which will flexibly mold itself to the shape of the ear canal.

Figure 4A:
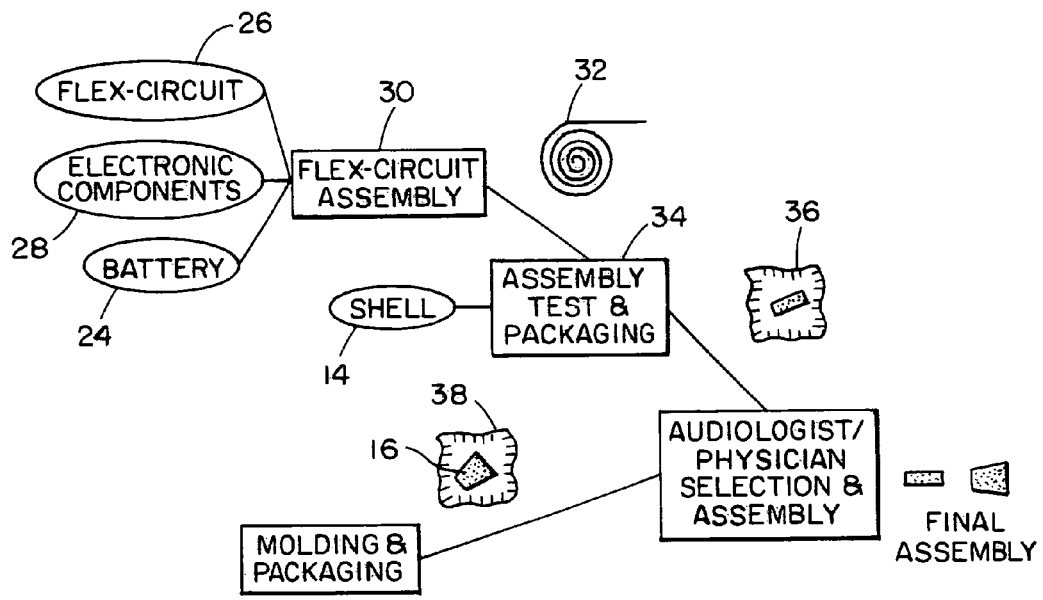
FIG. 4A is a flow chart diagram showing a method of assembling the hearing aid of the present invention.

Referring to FIG. 4A, there is illustrated a method of assembling the hearing aid 10 of the present invention. A flexible circuit 26 is fed from a reel along with the various components 28, which make up the assembly 12. Including microphones 18, receivers 22 and batteries 24, into an assembly apparatus 30. The assembly apparatus 30 assembles the components onto the flexible circuit to form a strip containing a plurality of the hearing aid electronics assemblies 12. The completed assemblies are mounted on a reel to form a reel 32 of the hearing aid component assemblies.

The flexible circuit assemblies of the reel 32 are then fed along with shells 14 into an assembler 34 where the electronics assemblies 12 are cut apart from the reel, and each electronics assembly 12 is formed and inserted into a shell 14. The shell assembly may then be inserted into a package 36, which is hermetically sealed and contains a gas, that protects the shell assembly from the atmosphere and extinguishes battery activity. The earmolds 16 are molded in a suitable molding apparatus and may also be packaged in hermetically sealed packages 38. The earmolds 16 are preferably molded in a few different sizes so that a suitable size can be used for each user of the hearing aid 10. Because the earmolds are formed from a compliant material one size of earmold may be appropriate for a number of different ear configurations.

Figure 5A:
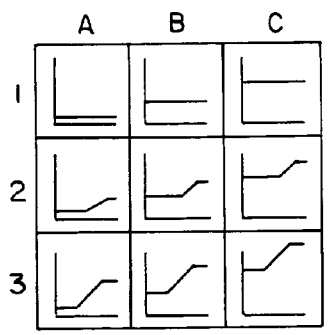
FIGS. 5A and 5B are charts showing the various responses of the amplifier circuit which can be used in a hearing aid according to the present invention.
Figure 5B:
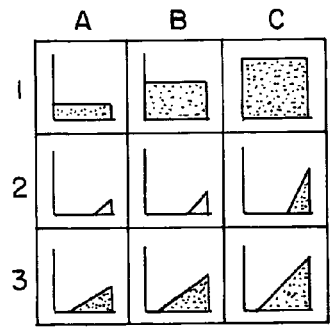

The signal processing circuitry 20 of the electronics assembly 12 may be designed, for example, to accommodate high-frequency hearing losses and flat-frequency hearing losses in the mild to moderate ranges. The signal processing circuitry 20 for different electronics assemblies 12 may be made to provide different audiological responses. FIGS. 5A and 5B are charts showing the various responses which may be provided by the different electronics assemblies 12 which are made in the process of the present invention. FIG. 5A shows the responses for a three-day device which has a fixed gain and frequency response, and FIG. 5B shows the responses for a 30-day device which has a two-channel amplifier. In each of FIGS. 5A and 5B, the columns represent different amplifier gains with column A being the lowest gain and column C being the highest gain. The rows represent different frequency response characteristics with row 1 being a flat response, row 2 a mild high frequency boost and row 3 the moderate high frequency boost. Thus, in making the signal processing circuitry 20, different components may be used so as to make up a fixed number of circuits having different gains and frequency responses as shown in FIGS. 5A and 5B. The different circuits are marked according to the charts of FIGS. 5A and 5B according to gain and frequency response, such as A1, A2, A3, B1, etc.

The last step in making the hearing aid 10 of the present invention is done by an audiologist or physician after the hearing of the user is tested and it is determined what type of audiological response is required of the hearing aid. The audiologist or physician checks the charts shown in FIGS. 5A and 5B and picks the signal processing circuitry 20 which will provide the audiological response required by the user. The audiologist/physician then picks the shell assembly, which contains the desired electronics, and picks an earmold 16 of the appropriate size for the user. The shell assembly is then inserted into the earmold 16 and the hearing aid 10 is ready to be inserted in the ear of the user.

Another alternative means of preventing air from degrading the battery while in storage is to use non-permeable packaging 38 (as shown in FIG. 4A) in lieu of a film tab on the battery or hearing aid. The following three materials are examples of such packaging:

1. Barex—made by Klockner-Pentaplast. It is a Barrier film designed to limit the transmission of $O_2$ & $CO_2$;
2. PVC with PVDC—made by K-P. It is a barrier film designed to limit $O_2$, $CO_2$ and $H_2O$; and
3. Alu-Alu—various manufacturers. It is a composite of Al and polyethylene that is heat sealable and is a barrier to virtually all gases and vapors.

All three films can be used exclusively or in combination. Most often, the packages are formed of plastic and aluminum (or a composite of aluminum and paper) as a lidding stock. Alu-Alu may be used for both the receptacle and the lid.

The non-permeable packaging is specially designed for the hearing aid to minimize any entrapped air. The package is desirably sized such that the hearing aid fits snuggly into it. The small amount of $O_2$ entrapped during packaging will react with the battery chemistry, but will have minimal impact on the life of the battery.

One advantage of sealing the hearing aid in the packaging is that the user does not need to remove any tape or seal from the hearing aid. If the tape on the hearing aid is used, however, the packaging may be further enhanced to assist the user of the disposable aid. In one embodiment, the packaging does not block $O_2$ and the hearing aid is sealed by a non-permeable tape applied to the battery or faceplate. This tape is also attached to the packaging. When the user removes the aid from the packaging, the tape is automatically removed and retained in the packaging.

Figure 4B:
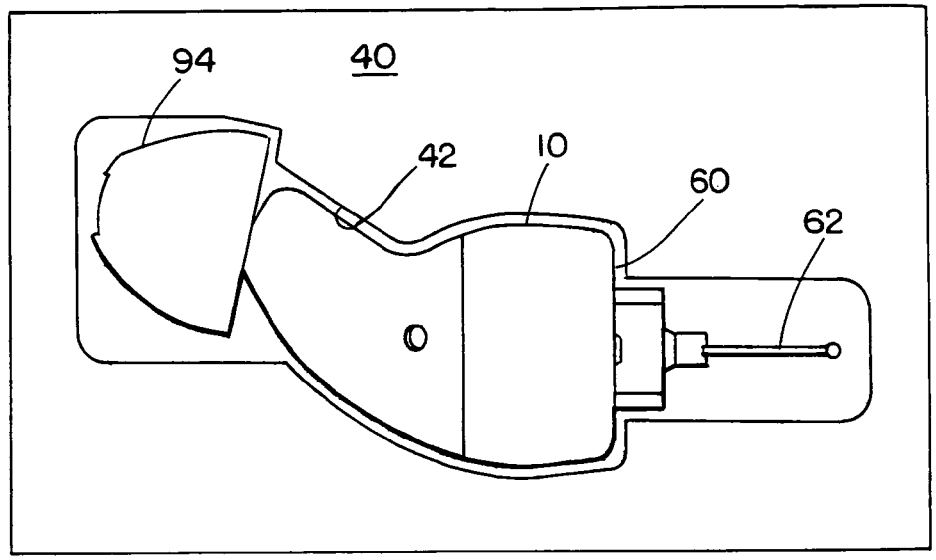
FIG. 4B is a plan view of packaging used to ensure inadvertent activation of the hearing aid during transport.
Figure 4C:
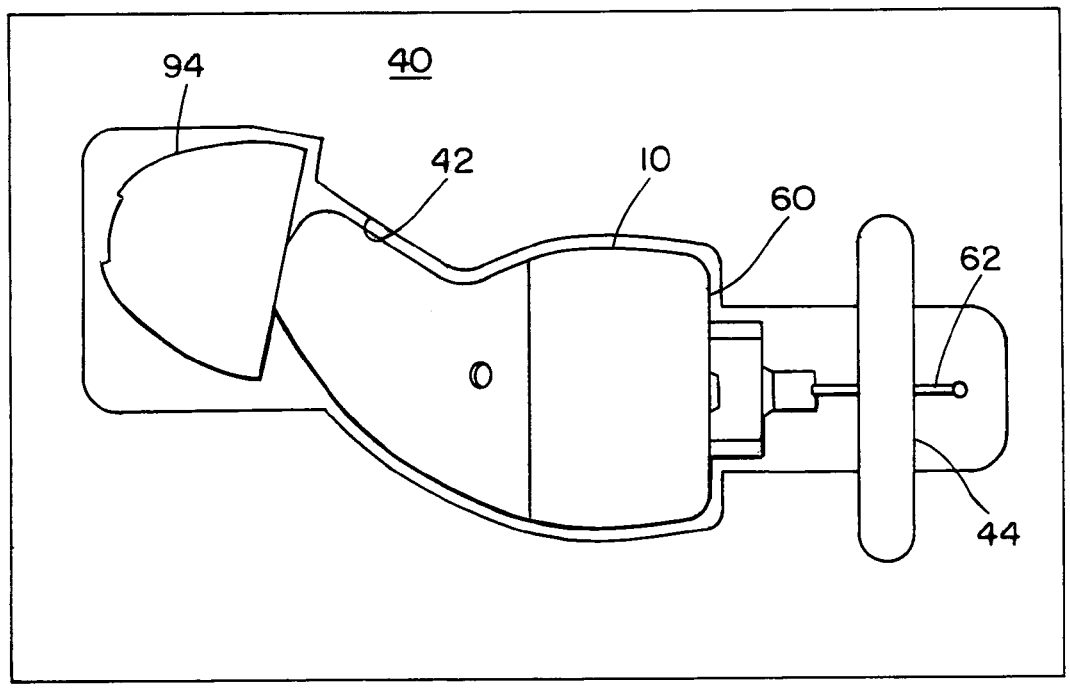
FIG. 4C is a plan view of alternative packaging used to ensure inadvertent activation of the hearing aid during transport.

The packaging preferably prevents the hearing aid 10 from being turned "on" during transport to prevent inadvertent degradation of the battery 24. In one embodiment, as shown in FIG. 4B, the packaging includes a housing 40 having a groove or slot 42 therein which preferably substantially conforms to at least a portion of the shape of the hearing aid 10. The groove 42 is substantially open adjacent the switch or pull cord 62 (the function of the pull cord to be explained below with reference to FIGS. 6B-6H; generally the pull cord is used to turn the hearing aid 10 "on" and "off" by pushing/pulling the cord into/away from the faceplate 60). Thus, the hearing aid 10 is snuggly held by the housing 40 to prevent the pull cord 62 from turning the hearing aid 10 "on", for example, by hitting a side of the housing. In another embodiment as shown in FIG. 4C, a securing member 44, for example, a strap, can be used to immobilize the pull cord 62 relative to the housing 40 to further prevent the cord from turning the hearing aid 10 "on".

An additional degree of battery protection and storage longevity may be achieved by eliminating $O_2$ and $CO_2$ during packaging and maintaining a 50% relative humidity. It is generally known that metal-air battery life is optimized if it is maintained at approximately 50% relative humidity. Lower humidity tends to dry out the electrolyte. High humidity allows absorption of moisture and dilution of electrolyte. Accordingly, maintaining 50% RH during the storage and use life of the battery, optimizes its potential.

Thus, it may be desirable to blow an inert gas, such as nitrogen, over the hearing aid while its package is being sealed. It may also be desirable to add a small amount of water to the nitrogen to maintain the humidity level at approximately 50% after the package is sealed.

In a hearing aid 10 according to the present invention, the signal processing circuitry 20 has fixed audio characteristics and is made in a limited number of acoustical formats. In addition, the acoustical format is preprogrammed in the electronics manufacture so that no potentiometers or other adjustable devices are needed for tailor the device for a particular user. In addition, in this first embodiment of the invention, the units are used only for the life of the battery. Thus, no on/off switch is used or required. Therefore, it is of simple design having a minimum number of components and is easy to assemble on an automatic basis. The signal processing circuitry 20 and the entire electronics assembly 12 is inexpensive because it can be easily made in large volumes to achieve economies of scale. The assembly 12 is encased in a simple hollow shell, which is easy to assemble by automated methods. Also, the earmold 16 is of simple design and of a soft, pliable material so as to be inexpensive. Thus, the entire hearing aid 10 uses a minimum number of inexpensive parts and is easy to assemble so that the hearing aid 10 is relatively inexpensive compared with presently used hearing aids.

Because the hearing aid 10 is so inexpensive, it can be disposable. Therefore, when the battery 24 of the hearing aid 10 is depleted, instead of replacing the battery 24, the whole hearing aid can be disposed of and replaced with a completely new hearing aid 10. Thus, there is provided by the present invention, a hearing aid 10 which is inexpensive to manufacture so as to be disposable. However, the hearing aid 10 still has all of the audio characteristics required by the user and has a high reliability. In addition, since it is disposable, it requires no service for major cleaning, repair and adjustment.

As set forth above, hearing aids commonly use metal-air batteries as a power source and in particular the zinc-air type of battery. Metal air batteries have the property that the oxygen in the air is the activator of the battery chemistry. As such, the battery is quiescent in the absence of air. Zinc-air cells are activated when air, and in particular oxygen, is allowed to enter the cell. In some zinc-air cells, a pull-tab covers one or more small openings that allow air to reach the air-cathode assembly. The pull-tab may be designed to allow air to diffuse slowly into the cell. With the pull-tab sealing the cell, the cell is oxygen deprived and may not support the same current as an unsealed cell.

A pull-tab that is impermeable to oxygen may be used to seal the air openings. Instead of an oxygen impermeable pull-tab, or in addition to such a pull-tab, the cell (battery) may be sealed in a nitrogen-filled, oxygen impermeable bag. The relative humidity of the nitrogen gas within the bag may be, for example, between 40 and 60 percent so as not to dry out the cell. When the sealed bag is opened or the pull-tab is removed, oxygen diffuses into the cell, the cell reverts to a zinc-air cell, and the voltage may increase, for example, from about 0.39 volts to more than 1.4 volts.

Another embodiment of this invention includes a non-replaceable metal-air battery sealed within the hearing aid. Nevertheless, a means is needed to allow airflow to the battery. An exemplary disposable hearing aid shown in FIG. 6A. A passageway 64 is provided on the face or cover plate 60 of the hearing aid 10, such that air may travel from the outside through the outer shell of the hearing aid to the cathode side of the battery 24. The passageway is a sealed volume, such that when the outer holes H are covered by a tape 59, no air is permitted to enter the passageway 64 and reach the air ingress holes 68 and into the cathode area 70 of the battery 24.

During storage or shipment, the disposable hearing aid may be exposed to an uncontrolled environment. Metal-air batteries are sensitive in their performance and life expectancy to the environment. Battery life is enhanced by minimizing exposure to $O_2$ or $CO_2$ during storage. Even when the battery is not coupled to a load, these gases may cause chemical reactions in the battery to degrade its life. It is therefore important to protect and seal the integrated battery in a disposable hearing aid from the environment. Traditional metal-air batteries use a non-air permeable tape over air ingress holes to protect the battery.

To assure that the air passageways do not reach the cathode side of the battery during storage or shipment, four different means for sealing the battery in accordance with the present invention can be provided:
1) sealing the battery with non-permeable tape applied to the air ingress holes on the cathode;
2) sealing the hearing aid with the non-permeable tape applied to air ingress holes on the faceplate;
3) sealing the hearing aid with non-permeable packaging; and
4) providing the hearing aid casing with a reclosable air-tight sealing device.

Figure 6A:
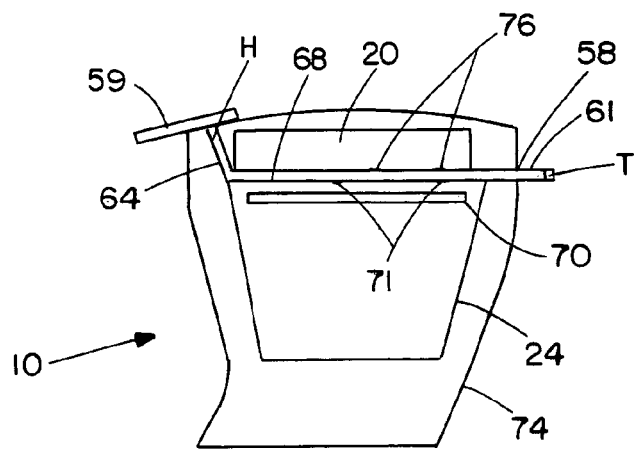
FIGS. 6A, 6B, and 6C are sectional views of an alternative embodiment of a hearing aid according to the present invention showing an on/off air block switch.

The simplest and most direct means of sealing a battery in a disposable hearing aid is by applying a non-permeable tape 61 to the battery 24, directly covering the air ingress holes 68 as shown in FIG. 6A. A disposable hearing aid which uses this sealing strategy is provided with a slot 58 in the shell 74, such that a tab T connected to the tape 61 on the battery 24 protrudes from the slot. When the user is ready to activate the unit, the tab T is pulled from the unit along with the tape 61 attached thereto exposing the battery's air ingress holes 68, and activating the battery. This embodiment also has the dual function of an "on" only switch as described below.

U.S. Patent Application entitled "MODULAR ELECTROACOUSTIC INSTRUMENT" by Leedom et al., application Ser. No. 09/250,512, is incorporated herein by reference for its teachings on disposable hearing aids. The referenced application describes a hearing aid having a removable tab that is used to seal the battery prior to use. In the exemplary embodiment of the invention, the removable tab 61 is positioned between the conducting contacts 76 on the bottom of the signal processing section 20 and corresponding contacts 71 on the top of the casing of the battery 24 to disconnect the battery 24 from the signal processing circuitry 20 until the tab 61 is pulled. The removable tab substantially seals the vent 68 in the battery casing. When the tab is pulled, oxygen is supplied to the battery through the vent and the battery is electrically connected to the hearing aid circuitry. As set forth in the above-referenced patent to Leedom et al. one or both of the contacts 76 and 71 may be spring contacts which make an electrical connection after the tab 61 is removed.

An alternative to putting tape on the battery is to put tape 59 covering the air vent holes 64 of the hearing aid. As described above with reference to FIG. 6A, a design feature of a disposable hearing aid according to the present invention provides for air passageways 68 to allow air to travel into the battery 24. For this approach to work, the battery 24 is desirably sealed in the hearing aid 10 so that no air can get into the battery except through specific passageways. Hearing aids typically have two passageways, a proximal passageway through which acoustic pressure waves interact with the microphone and a distal passageway through which the receiver produces acoustic pressure waves to activate the eardrum. In an embodiment of a hearing aid according to the present invention, the battery may be sealed from the air except for one of these passageways. The proximal passageway may be hermetically sealed to the battery or may be integrally molded to the faceplate so that the battery coming into contact with the faceplate forms a hermetic seal except for the proximal passageway.

Additionally, the distal passageway may be sealed to the battery with the use of a non-permeable adhesive or sealant. The proximal passageway 64 may be made from the housing material of the hearing aid (such as acrylic or Noryl) which connects the air holes in the faceplate with the air holes in the outer casing of the zinc air battery. Alternatively, the hearing aid shell itself may form a hermetic seal around the electronics and battery as described below with reference to FIG. 6B. With this design no special passageway is required. Air may only enter the unit in a controlled manner through specific air ingress holes.

With either of the alternative designs, a non-permeable tape 59 may then be applied over the holes in the faceplate. When the user is ready to activate and use the product, the tape is simply removed.

It is not generally known that a metal-air battery deprived of $O_2$ but under electrical load can deplete itself and have less than optimal energy capacity during use. In the case of a disposable hearing aid, even if non-permeable tape and/or packaging are used, if the battery is connected to the hearing aid electronics, the battery will self-discharge. Therefore, it is desirable to provide a mechanism to be incorporated in the hearing aid, to separate the electrical load from the battery during storage and shipment. There are several types of devices that can be used for this purpose.

One type of switch is an "on" switch that is an electrical contact, such that once the hearing aid is activated it cannot be turned "off". The simplest embodiment of this type of mechanism is to impose a non-conductive paper, tape or film 61 between one of the electrical contacts 76 of the signal processing circuitry 20 and the corresponding electrical terminal 71 of the battery 24, as shown in FIG. 6A. The hearing aid is manufactured with the paper or film 61 in place and extending out of the hearing aid shell 74. To activate the unit, the user pulls the tab T out allowing the contact 76 to touch the battery terminal 71, thus completing the electronic circuit. Replacing the film to turn the unit "off" is difficult, if not impossible. As described above, this tape may also be used to block the ingress of air into the battery so that, when the tape is removed, the battery is simultaneously activated and connected to the load.

A more traditional switch can also be incorporated. Non-disposable hearing aids typically have an electromechanical switch or the battery itself is used as the on/off switch. Since a disposable hearing aid does not have an accessible battery, an electromechanical switch can be used. The advantage of the on/off switch is that the unit can be turned "off" during storage and shipment, and in use, turned "on" only when needed. Having the ability to turn "off" the unit allows the unit to be inserted and removed from the ear without feedback because no sound is being amplified. Turning the unit "off" when not in use, also extends the battery life.

Another type of mechanism that can be used to extend battery life is an automatic switch, which monitors the battery voltage and turns the hearing aid "on" when the voltage is above some predefined value. As set forth above, in the absence of $O_2$, the metal-air batteries operate as zinc-hydroxide cells and have a lower voltage potential. During shipment and storage, the metal-air battery will have a tabbed non-permeable tape on the terminals and the voltage potential, as measured under small electrical load, should be less than 50% of the fully activated potential.

Figure 7:
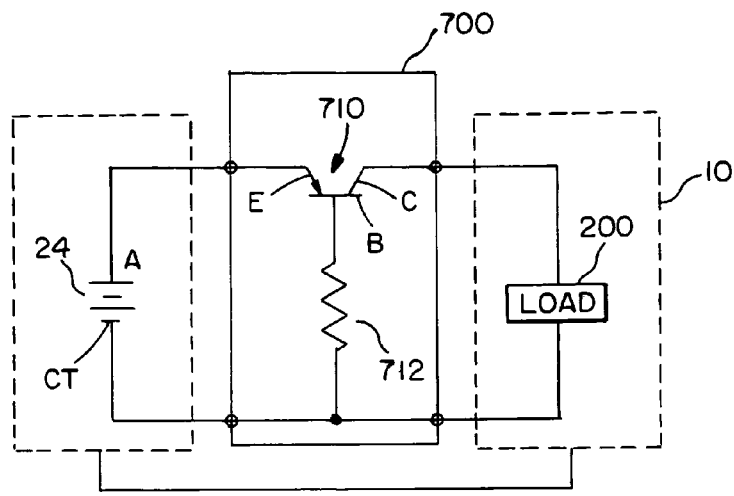
FIG. 7 illustrates an automatic "on" only switch for use with a pull tab seal on the battery of a disposable hearing aid.

An automatic "on" only switch is described for use with a pull tab seal on the battery of a disposable hearing aid in copending U.S. patent application Ser. No. 09/124,948 and entitled "Power Source For A Hearing Aid" by Sjursen et al., which is incorporated herein by reference for its teaching on power sources for disposable hearing aids. An exemplary circuit 700 coupled between a hearing aid battery 24 and a hearing aid load 200 in accordance with the present invention is shown in FIG. 7. The circuit includes a transistor 710 having its emitter electrode E coupled to the anode A of the battery 24. The collector C of the transistor is coupled to one terminal of the "load" 200 (i.e., the microphone electronics, signal processing circuit 20, and the receiver 22 of the hearing aid 10) and the cathode of the battery 24 coupled to the other terminal of the load 200. A resistor 712 connects the cathode of the battery 24 to the base B of the transistor 710. When the voltage provided by the battery is less than is required to turn on the transistor 710, the load 200 is disconnected from the battery 24 since the non-conducting transistor represents an open circuit between the load and the battery. However, when the voltage provided by the battery exceeds the turn-on voltage for the transistor 710, the transistor conducts current between its emitter E and collector C electrodes allowing current to be applied to the load 200.

This circuit 700 or a similar circuit can be incorporated into a hearing aid according to the present invention. When the hearing aid is manufactured, the battery is in a non-activated state. This is accomplished by one of the sealing means previously described. The circuit 700 continuously senses the potential of the battery 24 and prevents current flow to the signal processing circuitry 20 of the hearing aid until the unit is removed from its packaging and the battery is activated whereupon the voltage on the battery increases to its full potential. Upon sensing this voltage, the circuit 700 allows current to pass to the signal processing circuitry 20. The benefit of this circuit is that it eliminates the need and cost of an electromechanical switch. It also provides for hearing aid with longer shelf life and should be easier to use as the user does not need to turn on a mechanical switch or remove a mechanical barrier to connect the hearing aid electronics to the battery.

Figure 6B:
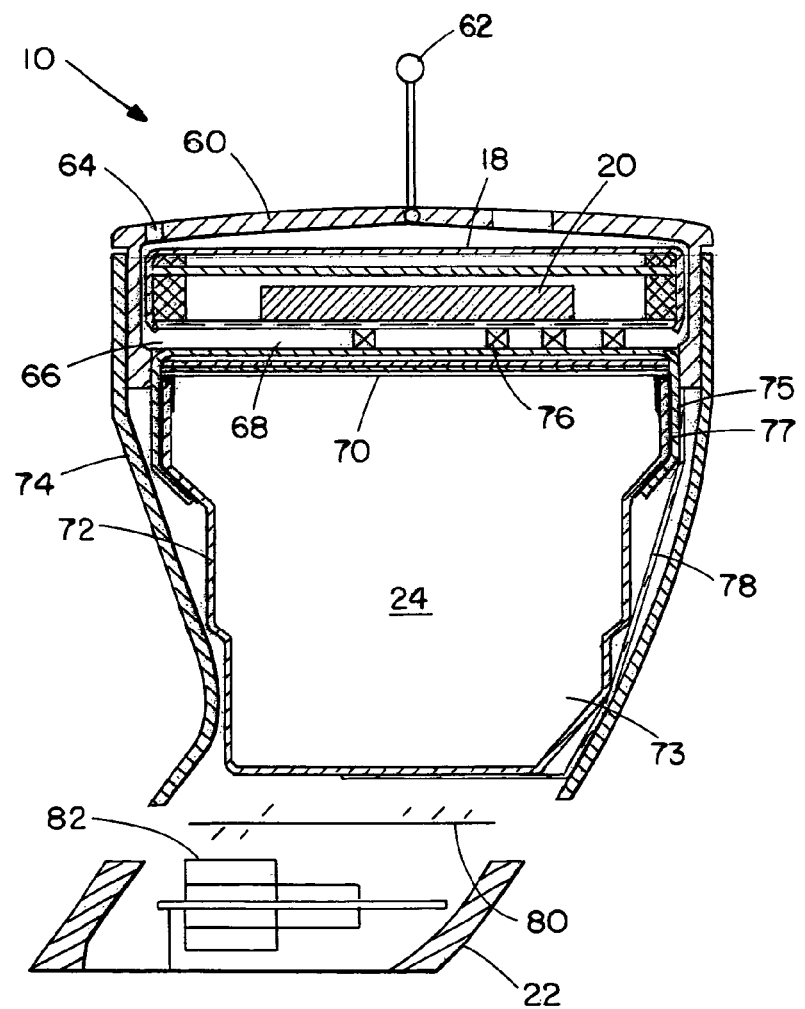
Figure 6C:
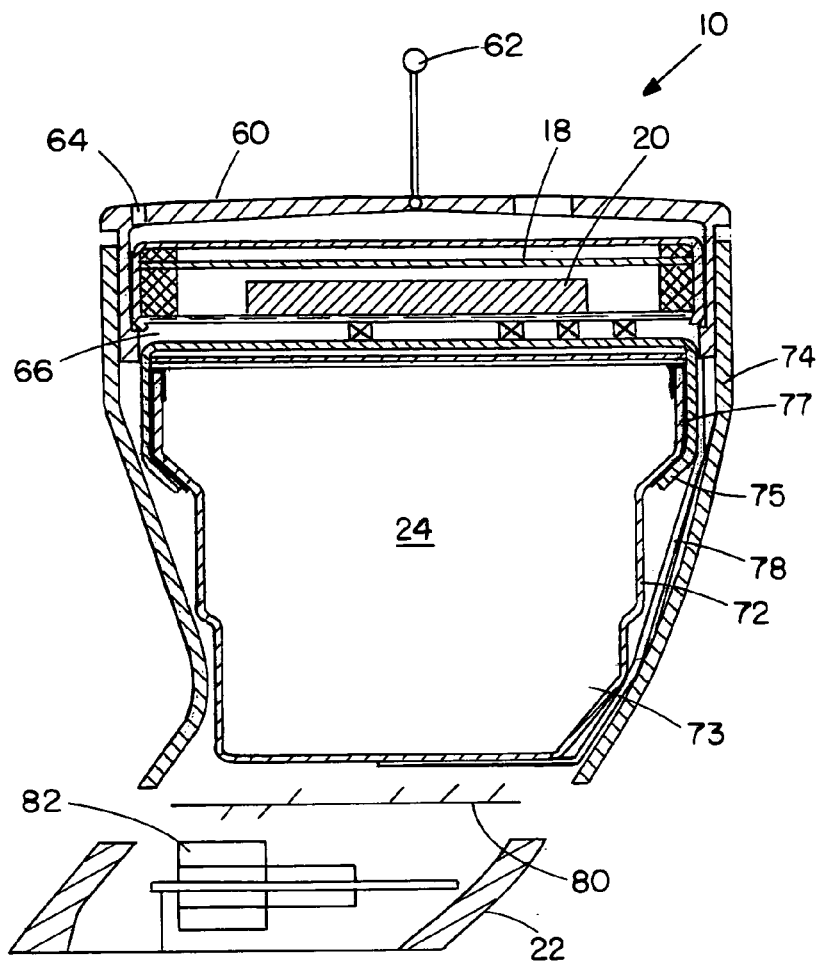
Figure 6D:
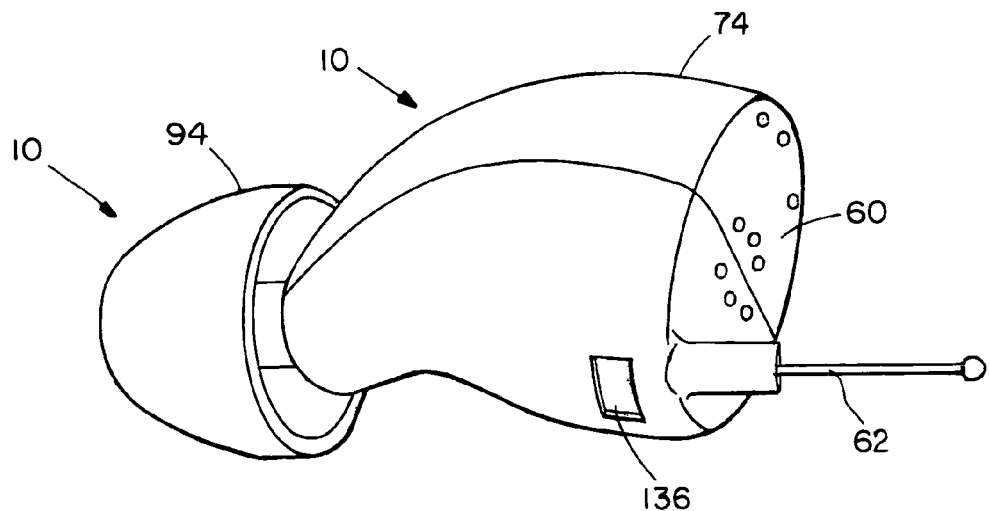
FIG. 6D is an isometric view of a hearing aid employing an alternative switch to turn the hearing aid "on" and "off"

An electronic switch, such as that disclosed above, may also be used with an air block switch to reduce oxygen and moisture transfer to and from the battery when the hearing aid is not being used. FIGS. 6B and 6C show one embodiment of a disposable in-the-ear (ITE) hearing aid 10 with an air block on/off switch.

FIG. 6B shows a disposable hearing aid having a modular construction. The hearing aid includes a faceplate 60 which protects the sensitive microphone 18, anchors a pull cord 62, and provides an opening 64 through which air may pass to the battery 24. The hearing aid also includes signal processing circuitry 20 which is connected to the microphone 18, and, via electrical circuit contacts 76 to the battery 24 and a flex circuit 78. The flex circuit 78 provides a connection between the signal processing circuitry 20 and the receiver 22. In this exemplary embodiment of the invention, the receiver 22 is manufactured separately from the battery 24 and signal processing circuitry 20. The receiver is coupled to the flex circuit 78 via a spring contact interface 80 which fits between the contacts 82 of the receiver 22 and the flex circuit 78. The battery 24 and signal processing circuitry 20 are permanently mounted in a plastic case 74. The battery includes a metal wall, which is also the anode of the battery, an electrolyte mixture 73 and a cathode grid 70. The battery is enclosed by a top cap 75 which is separated from the anode 72 by an insulator 77. An opening 68 in the top cap provides air from the air channel 66 to the cathode grid 70.

In one embodiment, as illustrated in FIG. 6C, the faceplate 60 is configured to slide in and out relative to the microphone 18 and hearing aid electronics 12. The plate 60 is pushed in, opening the air passage 66 when the user pushes the hearing aid into his or her ear. The faceplate 60 is pulled out, closing the air passage 66 when the user pulls the pull cord 62 to remove the hearing aid from his or her ear. When the plate 60 is pushed in, the air passage 66 is opened to allow air to enter the battery 24 via the opening 64 in the faceplate air passage 66 and battery air hole 68. When the plate 60 is pulled out, the air passage 66 is blocked as shown in FIG. 6C.

In accordance with other aspects of the present invention, it is desirable to conceal the hearing aid 10 is much as possible as there can be a stigma associated with wearing a hearing aid. This stigma may arise from the perception that those requiring hearing assistance are impaired and old. Thus, in one embodiment, the faceplate 60 of FIG. 6D may be formed from a substantially translucent or transparent material. The material can, for example, be "tinted" with a color(s) such as a flesh and root beer tones. When the hearing aid 10 is inserted into the ear canal for use, essentially only the faceplate 60 is visible. The translucent or transparent faceplate 60 picks up the natural color of the user's ear and helps conceal the hearing aid 10 within the user's ear. In another embodiment, the faceplate 60 may be formed with a reflective surface which can also help conceal the hearing aid 10. In yet another embodiment, the faceplate 60 may be formed with compound curves as shown in FIG. 6I to better reflect the contour of the user's ear.

Figure 6E:
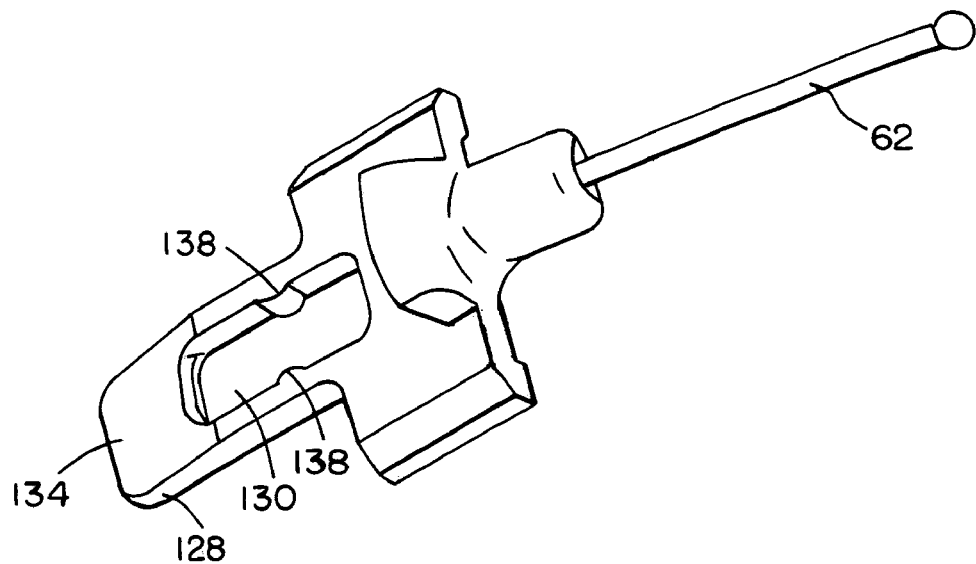
FIG. 6E is an enlarged perspective view of a pull cord and insulating member used to form the switch of FIG. 6D.

FIGS. 6D-6H illustrate another embodiment of a switch mechanism to turn the hearing aid 10 "on" and "off" in accordance with the present invention. Beneficially, the hearing aid 10 can be turned "off" when not in use to extend the life of the battery. In this embodiment, the pull cord 62 extends through the faceplate 60 and is connected to an insulating member 128, which can also be referred to as a slider, as shown in FIG. 6E. The insulating member 128, in one embodiment, is constructed from a plastic or other suitable material by an injection molding process. Insulating member 128 includes an aperture 130 therethrough and can also include a tapered leading edge 134 to facilitate its insertion into the hearing aid 10 during the manufacturing process. Preferably, the pull cord 62 is strong, but slender-so as to not be obtrusive in the user's ear, and fairly rigid. In one embodiment, the pull cord 62 is constructed from a monofilament nylon material. The pull cord 62 is thermally or otherwise bonded to the insulating member 128.

Figure 6F:
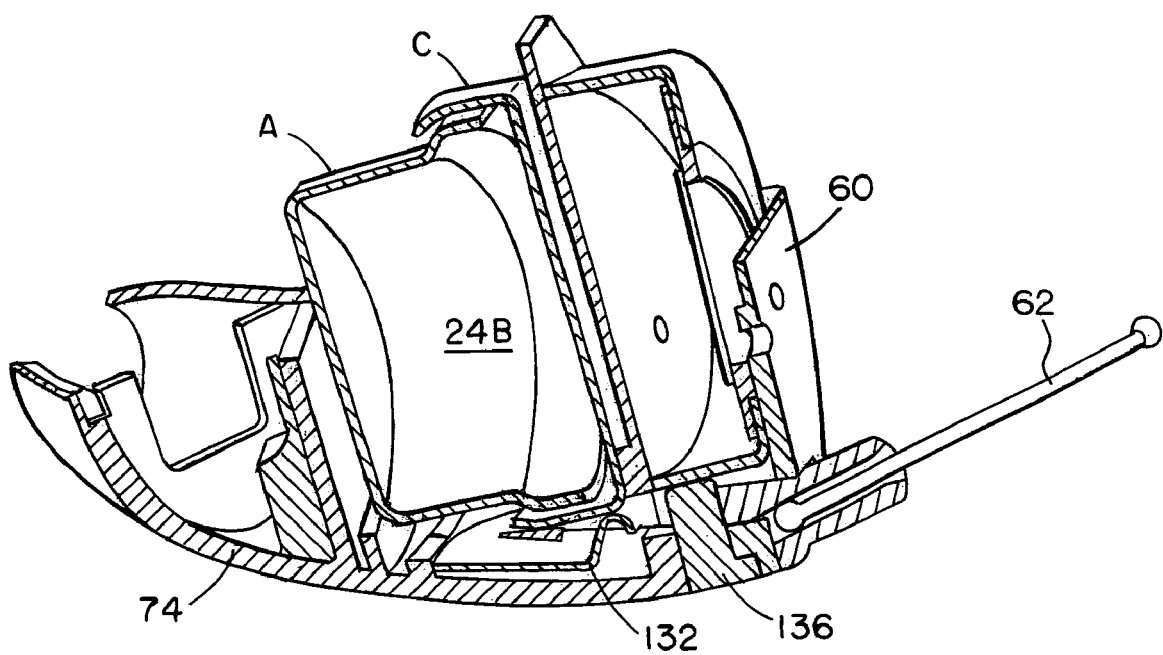
FIGS. 6F and 6G are partial isometric views illustrating "on" and "off" positions of the hearing aid of FIG. 6D.

FIG. 6F illustrates an "on" position of the hearing aid 10. In this position, the insulating member 128 permits a switch contact element 132 to contact the cathode C of the battery 24B through aperture 130. It is noted that the anode A and the switch contact element 132 are always electrically connected to the circuit board. In this "on" position, the insulating member 128 is inserted into the hearing aid towards the tip 94 and retained by stopping member 136.

Figure 6G:
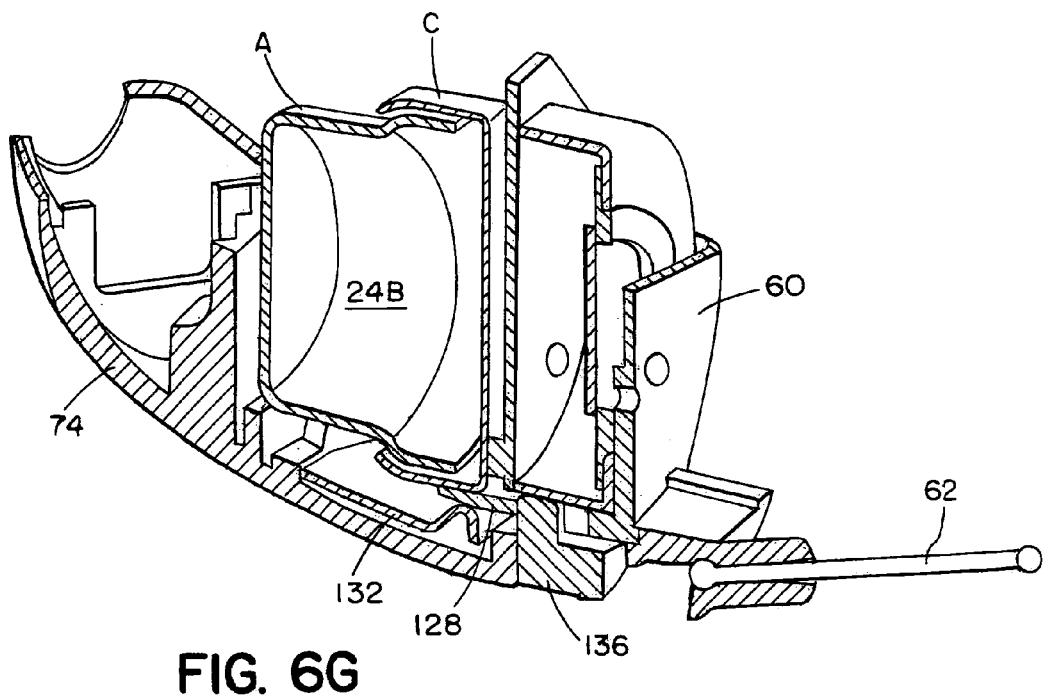

When the user pulls on the pull cord 62, the insulating member 128 is moved such that the switch contact element 132 is separated from the cathode C, as shown in FIG. 6G. As a consequence, the circuit between the battery and the circuit board is disrupted, thus turning the hearing aid "off". In this case, the stopping member 136 prevents the insulating member 128 from exiting the hearing aid 10.

Figure 6H:
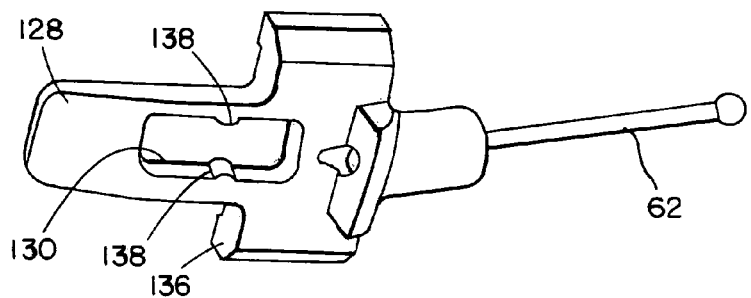
FIG. 6H is an enlarged perspective view of the pull cord and insulating member, as shown in FIG. 6E, and a stopping member of the hearing aid.
Figure 6I:
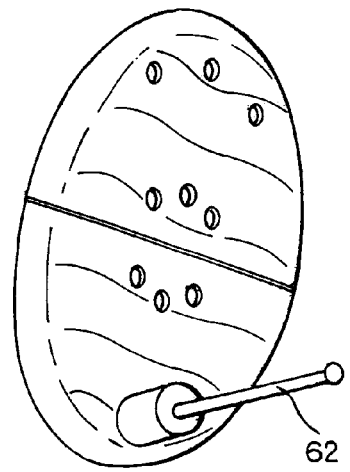
FIG. 6I is a partial end view of the hearing aid of FIG. 6D illustrating an alternative faceplate having compound curves.

As shown in FIG. 6H, the insulating member 128 preferably includes inwardly protruding members or detents 138 that allow the stopping member 136 to pass therebetween. The detents 138 temporarily "lock" the insulating member 128 in the respective "on" and "off" positions.

In a preferred embodiment, the hearing aid 10 is inserted and removed by the user holding the pull cord 62. Preferably, the motion of removing the hearing aid 10 turns the hearing aid "off" wherein the detents 138 allow the insulating member 128 to the position illustrated in FIG. 6G. When the hearing aid 10 is inserted into the ear, sufficient force is imparted to the insulating member 128 to turn the hearing aid "on". Thus, the motion of inserting and removing the hearing aid from the ear canal, respectively, turns the hearing aid "on" and "off".

Although the disposable hearing aid has been described thus far with a metal-air type battery a hearing aid can use other types of batteries. The primary advantage of these other batteries is their higher operating voltage. As the operating voltages of the battery drop below 2 volts, the design and fabrication of audio integrated circuits becomes increasingly difficult.

The primary disadvantage of non-metal-air batteries is their reduced energy capacity. Typically, metal-air batteries have twice the capacity of non-metal-air batteries.

When a disposable hearing aid utilizes a non-metal-air battery, the issues for sealing and providing an air passageway are eliminated. Improved acoustical performance can be achieved. However, the expected usage life would be about half that of a metal-air battery.

Figure 8A:
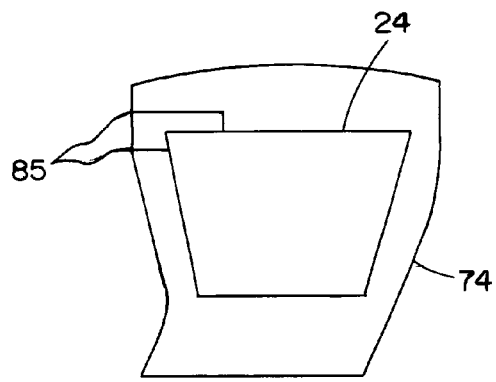
FIGS. 8A-8C illustrate a hearing aid having a rechargeable battery.
Figure 8B:
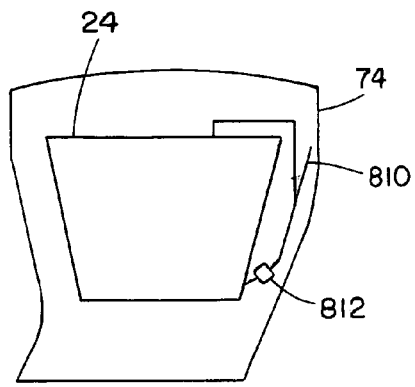
Figure 8C:
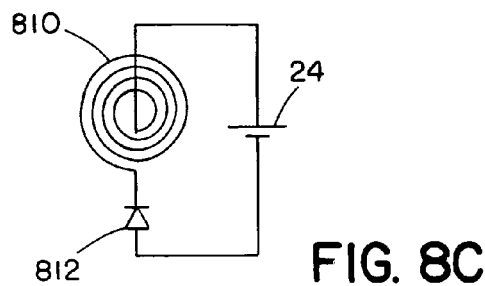

A disposable hearing aid can also utilize a rechargeable type battery as shown in FIGS. 8A and 8B. The rechargeable type battery can be sealed within the unit. However, means are added to the unit to permit external energy transfer to the battery for recharging. This can be done by providing external battery contacts 85, as shown in FIG. 8A to allow direct electrical conduction or by providing an energy transfer device, such as an inductive coil 810, as shown in FIG. 8B, or a photocell (not shown) to allow the battery to be charged from an induced alternating current (AC) or light source. In all cases, the battery would be charged when it is not in use, for example, overnight. In one possible configuration, the hearing aid may be provided with a charging unit (not shown) which provides a regulated direct current charging potential to the direct electrical contacts 85 or which provides a regulated alternating current potential to an induction coil (not shown) in the charging unit. If the hearing aid includes external battery contacts 85, then the charging of the battery is entirely under control of the charging unit. If the hearing aid is inductively coupled, however, the hearing aid may include a rectifier 812 in addition to the induction coil 810 to convert the induced AC potential into a DC potential which is applied to charge the battery 24, as shown in FIGS. 8B and 8C.

An advantage of using rechargeable batteries, is that the overall life of the unit may be extended, making it more economical. In addition, the voltage potential of rechargeable batteries may be higher than that of metal-air batteries allowing more flexibility in the design of the electronic circuitry and improved sound quality. For example, rechargeable lithium metal battery has an operating voltage of 3 volts compared with 1.3 volts for zinc air.

Figure 9:
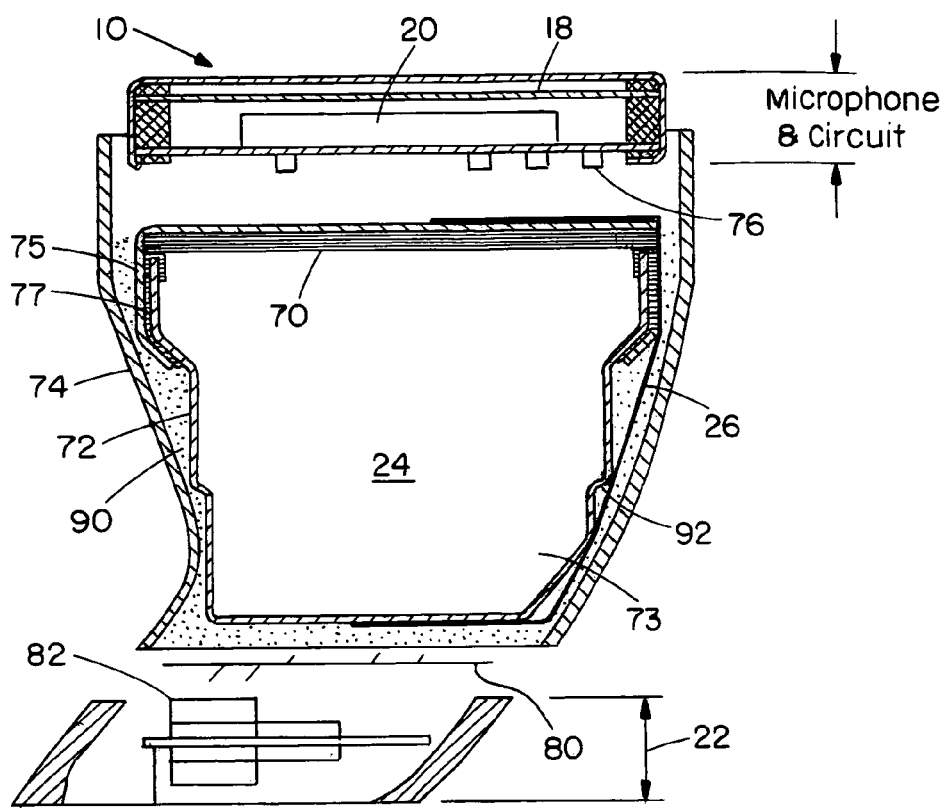
FIG. 9 is a sectional view of an alternative embodiment of a hearing aid in accordance with the present invention particularly illustrating an inventive power source.

FIG. 9 illustrates another embodiment of hearing aid 10, which can be disposable or nondisposable. As illustrated, the battery 24 separates the microphone 18 from the receiver 22 to minimize acoustic feedback between the same. To obtain the maximum life from the battery 24, the housing for the battery conforms closely to the internal shape of the ear canal. In one embodiment, the battery comprises a plastic material which has been found to be comfortable material when inserted in the ear canal. In another embodiment, the housing or wall of the battery 72 comprises a metal material. A sealant 90 can be injected between the battery wall 72 and the plastic shell 74 to minimize feedback between the microphone 18 and the receiver 22 and to keep the battery 24 from rattling against the shell.

As shown, battery 24 includes at least one step 92 such that the overall shape of the battery substantially conforms to a portion of the ear canal between the aperture and the first bend. This allows the battery life to be extended by increasing the total zinc volume. The electrical connection from the anode and receiver to the circuit in the microphone section can be an adhesive backed single-sided flex circuit applied to the side of the battery individual wires, metal rods, traces printed onto an insulated battery wall, or other suitable means. A spring contact interface plate 80 completes the circuit between the receiver 22, anode, and the flex circuit 26 on the battery.

Zinc-air cells are commonly deployed for hearing aid applications for the reasons that include: (1) they possess the highest capacity-to-volume ratio of any miniature batteries, (2) their discharge curves are relatively flat, (3) compared to mercuric oxide and silver oxide batteries, the zinc-air cells exhibit a more stable voltage of high currents, and (4) circuit design is facilitated by the essentially constant internal resistance of the batteries. Having a nominal voltage of 1.4 V, zinc-air batteries must have access to oxygen to operate properly.

Figure 10:
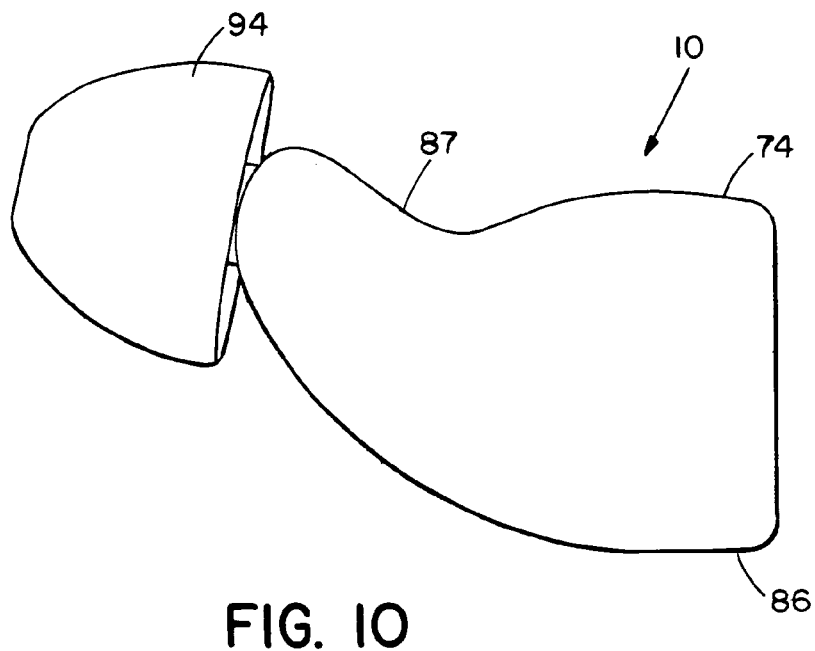
FIG. 10 is a plan view of an embodiment of a hearing aid in accordance with the present invention.

FIG. 10 illustrates a preferred embodiment of a hearing aid 10 generally illustrating the overall shape of the mushroom-shaped tip 94 and two half-shells 74 joined together. The two shells 74 form a generally oval cross-sectional base portion 86 which extends into an elongate curved middle section 87. The oval preferably varies in size progressing toward the middle section 87. In one embodiment, the two half-shells 74 are sometimes referred to as "clam shells". In assembly of the hearing aid 10, the components are inserted into one or both of the clam shells, and the shells are subsequently glued, cemented, snapped (or a combination thereof) together.

Figure 11:
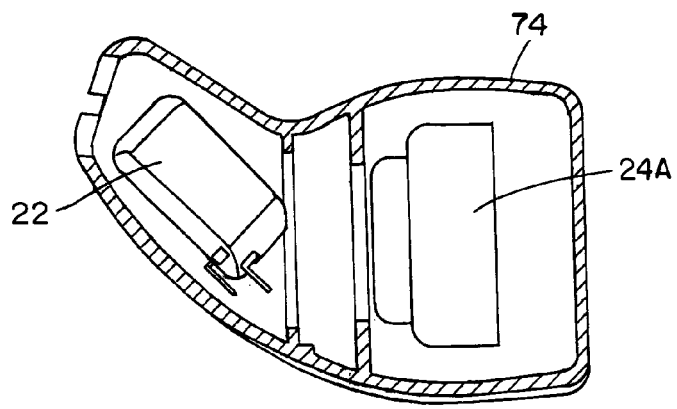
FIG. 11 is a partial cross-sectional view of the hearing aid of FIG. 10.

FIG. 11 is a cut away side view of one of the shells 74 which houses the receiver 22 battery 24A and the microphone 18. Two such shells 74 are joined together to complete the housing. The battery 24A shown in FIG. 11 is a standard zinc-air cell which has a substantial cylindrical geometry. Typically, the construction of these zinc-air cells consist of an air cathode can, an anode can, insulators, and an electrolyte. It is noted that the cathode and anode cans, which are coated with nickel to resist corrosion and to ensure good electrical contact, are separated by a nylon insulator. The cathode, which is electrically connected to the cathode can, is constructed from catalyzed carbon, which serves to reduce oxygen from the air. Alternatively, the anodes are gelled mixture of amalgamate zinc powder and electrolyte, which is typically a highly conductive solution of potassium hydroxide (KOH) in water.

The battery 24A illustrated in FIG. 11 is a conventional 312 zinc-air cell which has been found to be the largest conventional cell that would fit inside of the battery compartment formed by the two half-shells 74.

Figure 12:
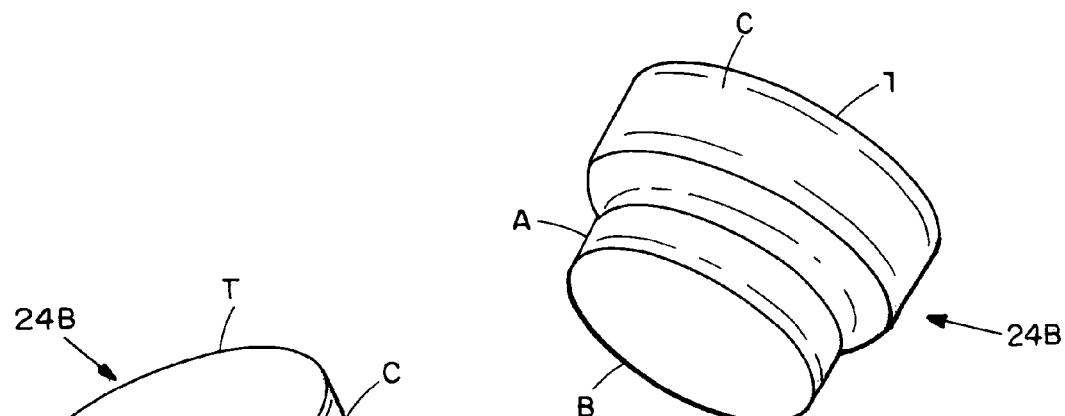
FIG. 12 illustrates an embodiment of an inventive battery particularly showing the bottom of the anode can.
Figure 13:
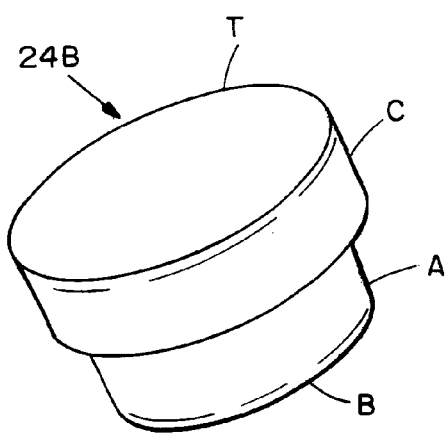
FIG. 13 illustrates the inventive battery of FIG. 12 particularly illustrating the top of the cathode can.

A custom made battery 24B in accordance with the present invention is illustrated in two perspective views of FIGS. 12 and 13. More particularly, FIG. 12 shows the bottom B of the anode A while FIG. 13 illustrates the top T of the cathode C. It is noted that relative to the conventional zinc-air cell, the anode can is lengthened and tapered. The tapering is actually a slight draft that is consistent with normal manufacturing processes for zinc-air cells. Additionally, the radial dimension of the battery has been increased to better fill the available cavity in shells 74.

Figure 14:
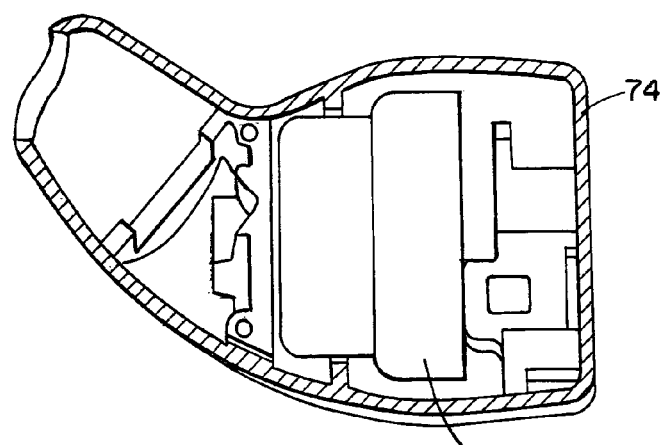
FIG. 14 illustrates the inventive battery of FIGS. 12 and 13 positioned in the hearing aid shells in accordance with the present invention.

To facilitate the change in the radial dimension, the cathode can height has been minimized so as to reduce the adverse, double-packaging affect attributable to the anode can, insulator, and cathode can construction. As inferred from FIG. 14, if a full-height cathode can were used, the radial dimensions of the anode can would have to be smaller than proposed, and consequently, the capacity of the custom battery would necessarily be reduced. Therefore, the height of the cathode can is as small as possible while still maintaining an adequate seal. The net effect of these changes may be observed by comparing FIG. 14 to FIG. 11. It is seen that the custom battery 24B occupies a much larger fraction of the space available for the power source. In fact, by calculating the volumes of the custom battery 24B and comparing it to the standard 312 24A cell, a quantitative measure of the increased capacity may be obtained. In doing so, a volume of 0.01757 $in^3$ for the custom battery was calculated that is contrasted to the 0.008719 $in^3$ volume of the standard 312 cell. Since the battery volume has increased by over 100%, the life of the hearing aid will approximately double.

Figure 15:
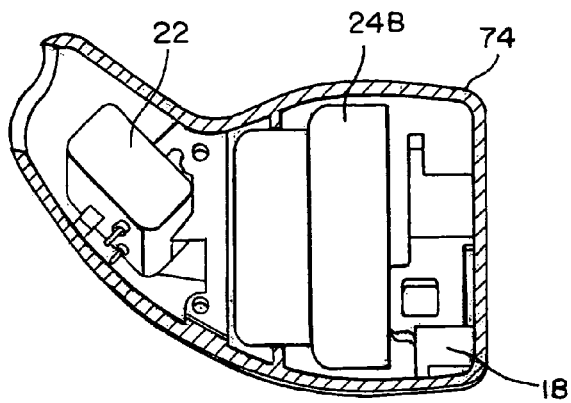
FIG. 15 is similar to FIG. 14 which further includes the receiver and microphone position within the shells.

FIG. 15 illustrates the custom made battery 24B inserted into shell 74 with the microphone 18 and receiver 22 in place.

Figure 16:
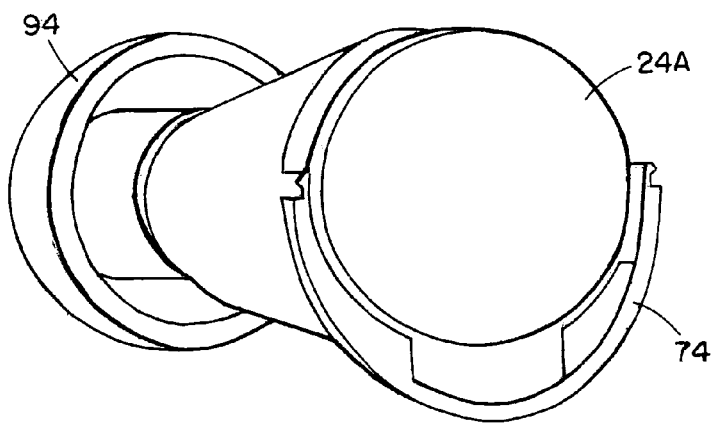
FIG. 16 is a cross-sectional view of a hearing aid in accordance with the present invention particularly illustrating the cross-sectional shape of one embodiment of the battery.
Figure 17:
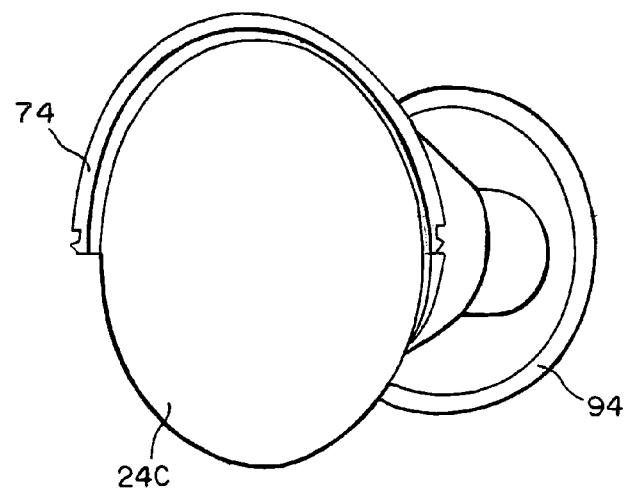
FIG. 17 is a cross-sectional view of another embodiment of a hearing aid in accordance with the present invention particularly illustrating an elliptical cross-sectional shape of an alternative battery.

FIG. 16 is a partial cross-sectional view showing the custom battery 24A within a half-shell 74. It is noted that half-shell 74 has a generally elliptical shape. Accordingly, in another embodiment of the present invention, the battery 24 can include a generally elliptical cross-sectional shape to fill substantially all of the available volume within shells 74. This is illustrated in FIG. 17, i.e., a custom made battery 24C having a generally elliptical cross-sectional shape.

Figure 18:
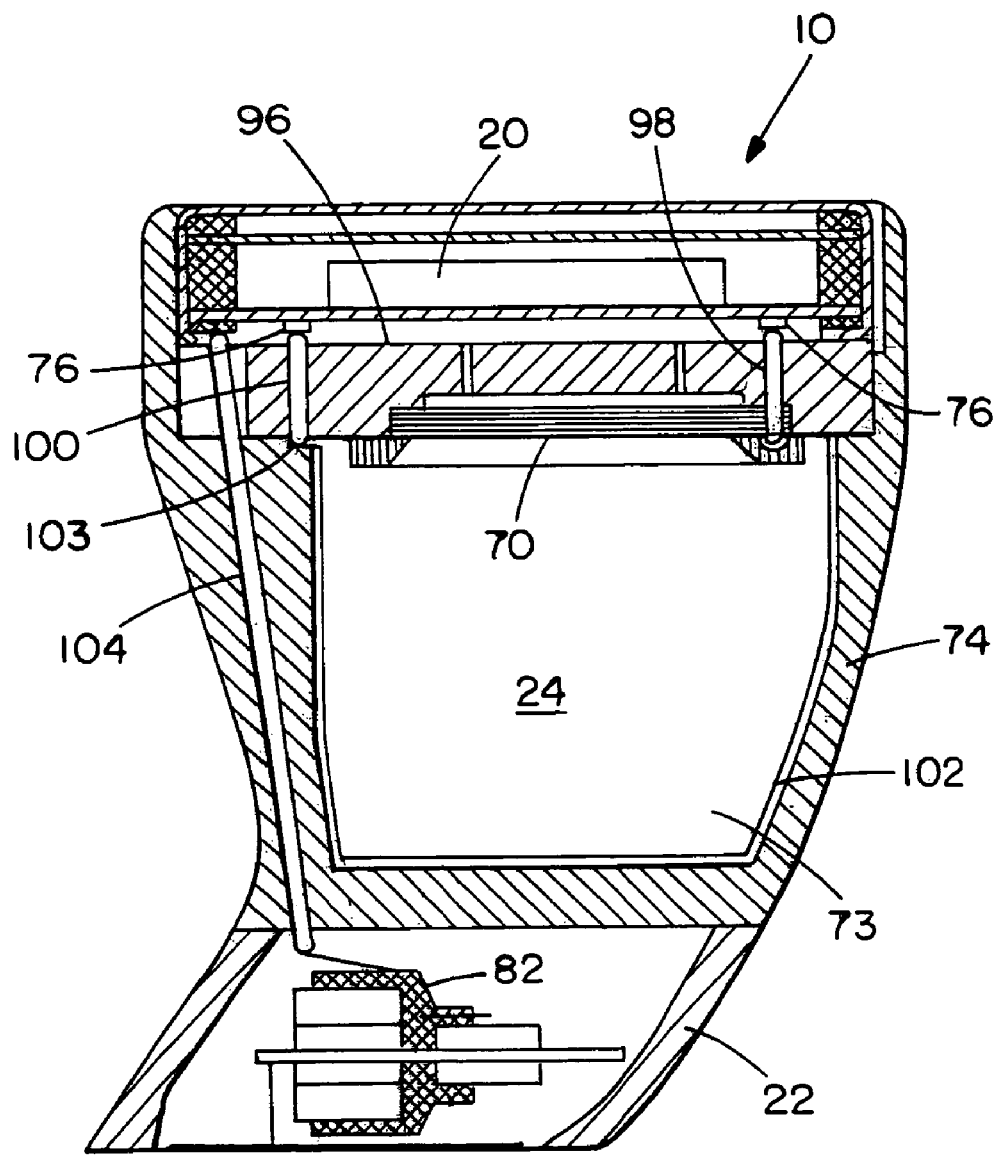
FIG. 18 is yet another embodiment of a hearing aid in accordance with the present invention particularly illustrating a plastic battery.

FIG. 18 illustrates another embodiment of hearing aid 10 wherein the battery housing is formed of plastic. A plastic cathode plate 96 contains two or more insert molded conductive pins 98, 100 that carry the battery power to the circuit 20 in the microphone section 18. One or more pins 98 penetrate the cathode grid 70 at various locations for one battery connection. One or more pins 100 press onto tabs 103 on the metal shell 102 to make the anode connection. All the pin connections are preferably spring-loaded or use other means such as conductive adhesive to ensure a reliable contact. The zinc and electrolyte 73 are contained in a metal expandable shell 102 that serves as an anode. The expandable feature allows the zinc to expand without breaking the plastic housing 74 as the zinc is converted into zinc oxide.

The plastic housing 74 contains at least two conductors 104 to connect the receiver 22 to the circuit board in the microphone section 18. In one embodiment, these conductors 104 can be insert molded into the walls of the battery 24 or dropped into a cavity molded into the walls of the battery. The connectors over pins 104 make a spring contact with the receiver contacts 82. Preferably, the battery assembly has a total of four contacts slightly above the surface of the cathode plate 96. These contacts preferably interface with spring connections 76 on the circuit board.

Figure 19:
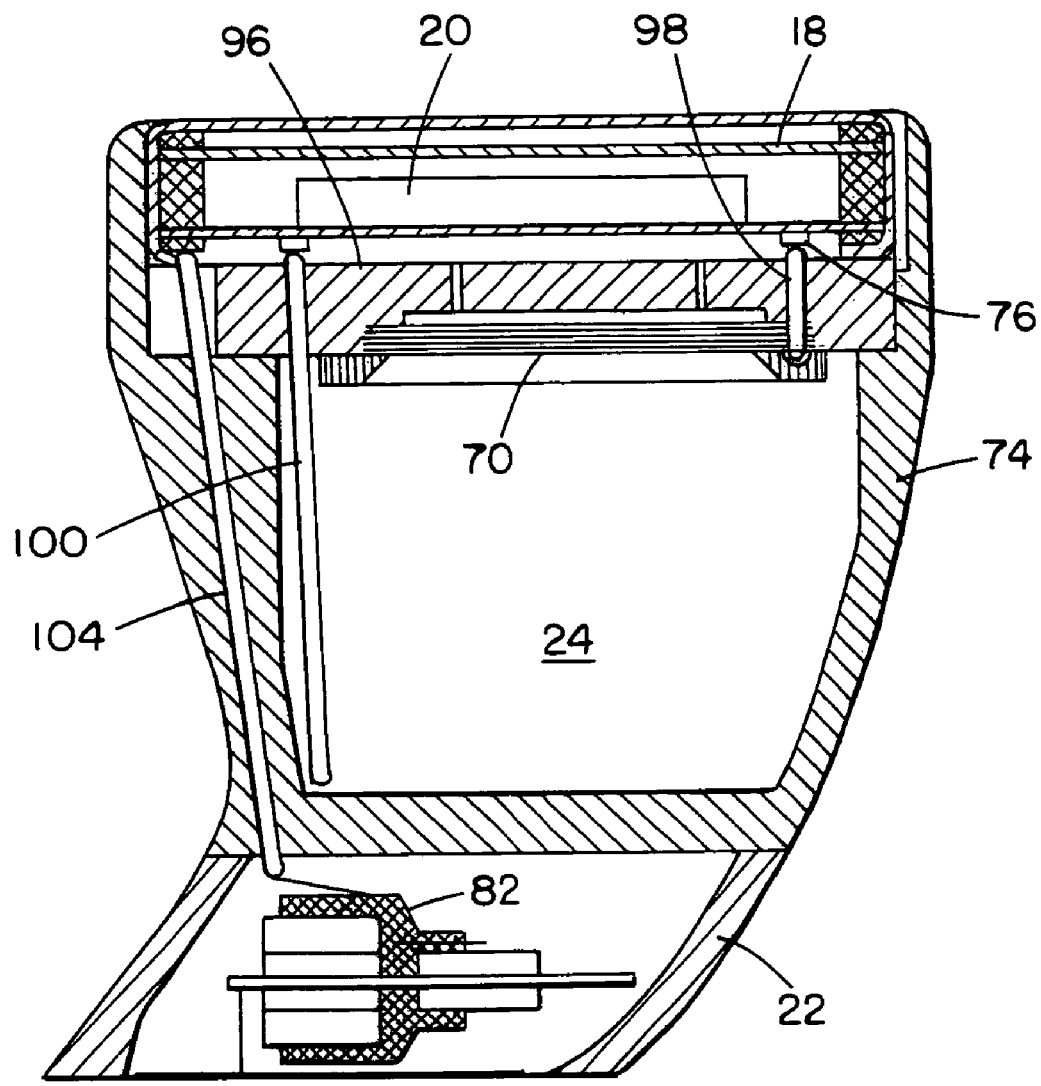
FIG. 19 illustrates a further embodiment of a hearing aid in accordance with the present invention particularly illustrating an alternative anode design.

FIG. 19 illustrates an alternative anode design in accordance with aspects of the present invention. One or more rods 100 injection molded into the cathode plate 96 replace the metal shell 102. Preferably, the rods 100 are pushed into the zinc as the cathode plate 96 is sealed into the plastic housing 74.

In one embodiment of the present invention, it is preferable to automate the assembly of the hearing aid as much as possible to reduce manufacturing costs. One aspect of the present invention is to provide a quick-connect mechanism for simultaneously interconnecting, for example, the receiver and the battery, without soldering or welding such small parts or contacts. The term "simultaneously" is understood to mean to occur at the same time. Thus, the necessary electrical contacts are completed by the quick-connect mechanism at the same time.

Figure 20:
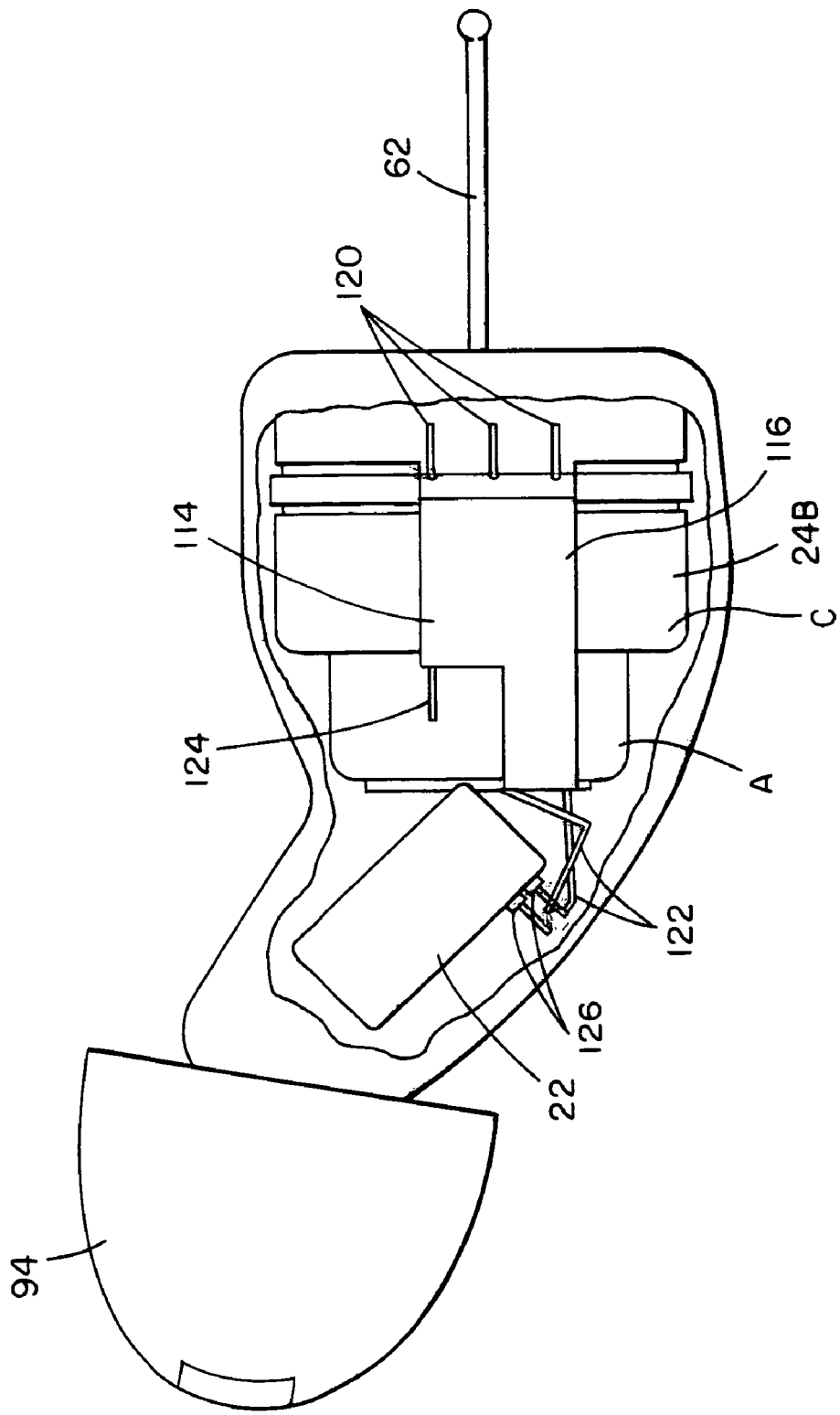
FIGS. 20 and 21 illustrate an embodiment of a quick-connect mechanism for use in a hearing aid of the present invention.
Figure 21:
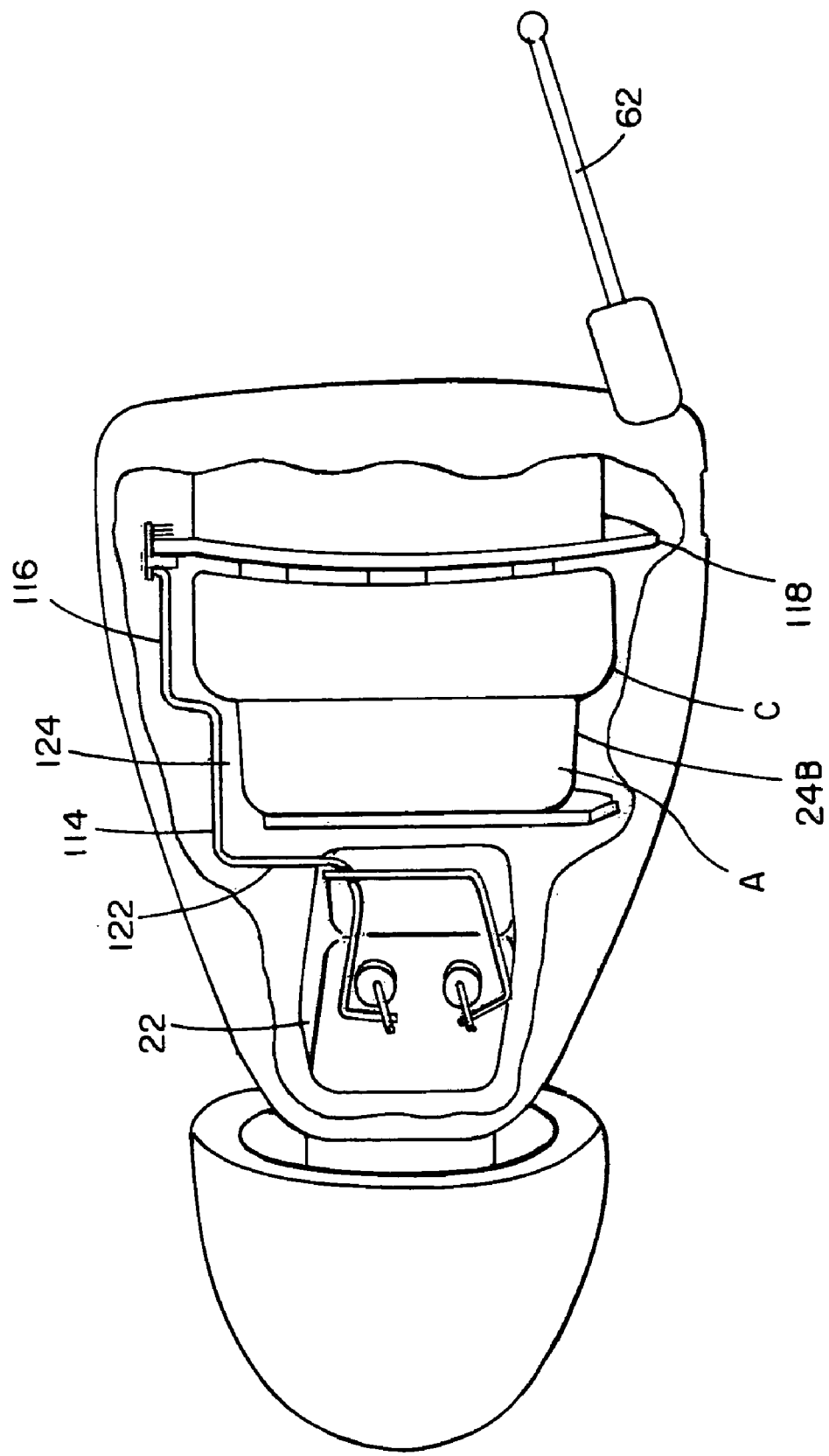

FIGS. 20 and 21 illustrate an embodiment of a quick-connect or coupling mechanism which includes a saddle member 114 which is preferably formed from a non-conductive material, such as plastic. Saddle member 114 supports at least one contact member 116 which interconnects the anode A of battery 24B with the circuit board 118 in the microphone section. Saddle member 114 further supports at least one contact member 122 which interconnects the cathode C of battery 24B with the receiver contacts 126. A battery contact 124 connects the anode A to the contact members 116, 122. Preferably, the contact members 116, 122 are insert molded leaf springs having twisted ends 120 which increase the contact pressure to ensure a good electrical connection.

In one embodiment, all of the internal components including the battery 24B, the receiver 22, the microphone 18, and tip 94, are placed within a first or bottom half-shell 74. The saddle member 114, which includes contacts members 116, 122, is placed on top which completes all the necessary interconnects between the components. The second or top half-shell 74 is preferably snapped and cemented onto the bottom half-shell to form the hearing aid 10. In an alternative assembly sequence, the saddle member 114 is positioned within the top half-shell 74 before the top shell is installed onto the completed lower shell assembly. Comb features (not shown) are preferably added to the top half-shell 74 to guide the spring ends 120 and to back up the receiver 22 to prevent bending damage as the spring contact applies its force. Preferably, the twisted ends 120 have an antioxidant grease or a gold plate thereon to ensure long-term contact reliability.

Generally, battery life is often determined by how often the hearing aid 10 is used, if the hearing aid is used frequently. In the case of infrequent use, the battery life can be limited given that the battery can dry out and become nonfunctional if exposed to low humidity, or become bloated and become nonfunctional if too much moisture is absorbed due to exposure to high humidity. Thus, in accordance with one aspect of the present invention, the use life of the hearing aid 10 can be extended by providing more than one battery which can be activated, preferably one battery at a time. Multiple batteries can be used in any hearing aid device, including disposable and non-disposable in-the-canal (ITC), completely-in-the-canal (CIC), and behind-the-ear (BTE) type hearing aids.

Figure 22:
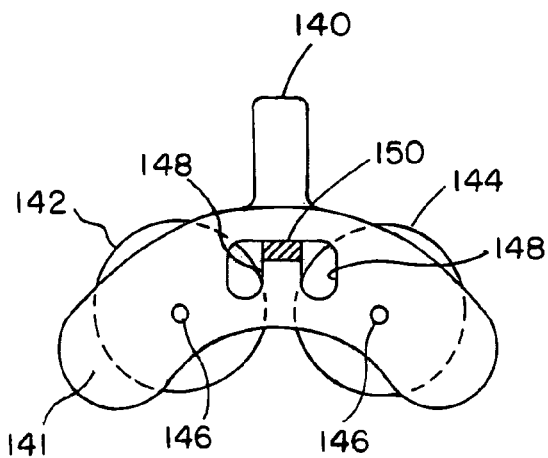
FIGS. 22 and 23 are schematics of a switch mechanism used to select and activate a hearing aid battery.
Figure 23:
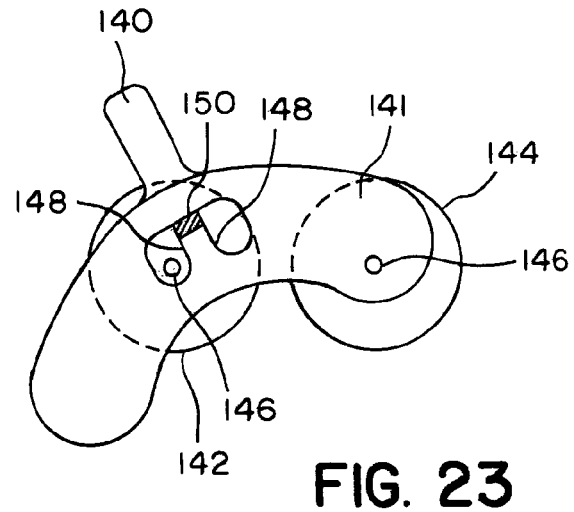

FIGS. 22 and 23 illustrate one embodiment of a switch device for use in a hearing aid 10 having multiple batteries which can be sequentially activated. The switch device 140 is positioned adjacent a first battery 142 and a second battery 144. In FIG. 22, the switch 140 is in the "off" position with an insulating member 141 of the switch covering a portion of each battery 142, 144. In this position, each battery 142, 144 is electrically connected to ground and neither battery 142, 144 is electrically connected to the circuit board of the hearing aid 10. Each battery 142, 144 includes a hole 146 which, when exposed to air, becomes activated. In the "off" position of FIG. 22, the switch 140 covers both holes 146.

When the switch 140 is moved towards one of the batteries, for example, battery 142 (see FIG. 23), the battery hole 146 is exposed to air via an aperture 148 of the insulating member 141. At or about the same time, the battery 142 is electrically connected to the circuit board to power the hearing aid 10. In one embodiment, the switch 140 includes an electrical conducting member 150 which completes the circuit to the circuit board to power the hearing aid 10. Thus, the switch 140 can be used to both turn the hearing aid 10 "off" and "on" and select a battery that is used to power the hearing aid.

Figure 24:
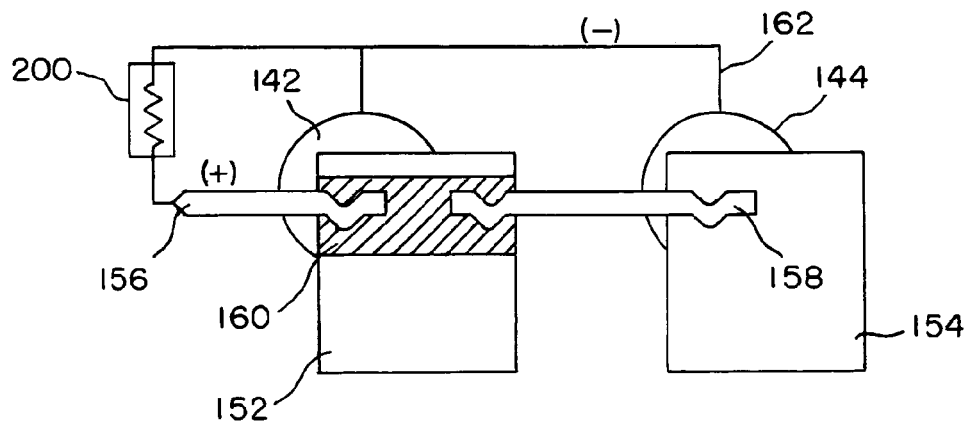
FIG. 24 is a schematic of an alternative switch mechanism used to select and activate a hearing aid battery.

FIG. 24 is an alternative embodiment of an apparatus for selecting and activating a battery. In this embodiment, a first insulator 152 and a second insulator 154 are positioned adjacent respective batteries 142, 144. As in the previous embodiment, each battery 142, 144 is connected to ground. In the "off" position, insulators 152, 154 separate respective electrical conductors 156, 158 from batteries 142, 144 to break the circuit 162 to the hearing aid load 200. Insulator 152 includes a conductive strip 160 thereon which completes the circuit between battery 144 and the load 200 when insulator 154 is moved allowing the conductor 158 to contact the battery 144. When battery 144 has expired, conductor 152 is moved to allow conductor 156 to contact battery 142. Preferably, only a single battery is connected at a given time to the circuit 162. Otherwise, if the first battery is not disconnected after use, its lower voltage puts an electrical drain on the second battery, shortening its life. Thus, when insulator 152 is moved, the battery 144 is disconnected from the circuit 162.

Figure 25:
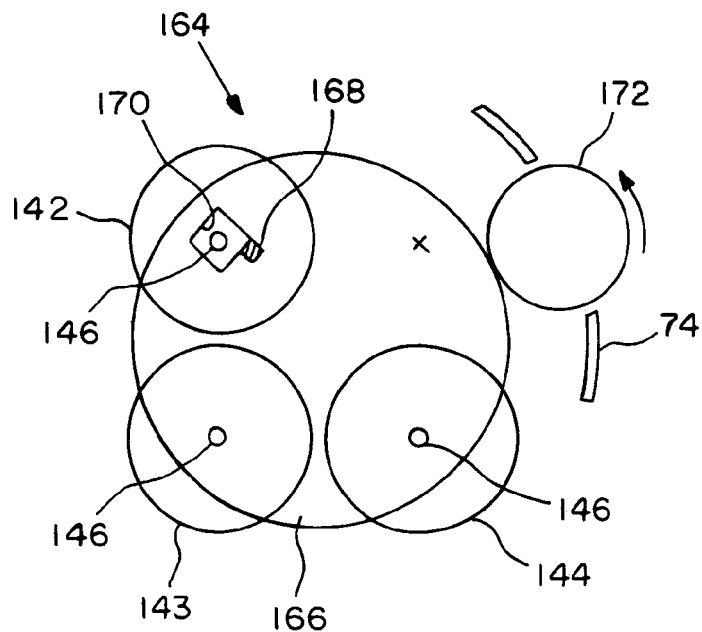
FIG. 25 is a schematic of another alternative switch mechanism used to select and activate a hearing aid battery.

FIG. 25 illustrates an embodiment of a switch mechanism 164 for selecting a battery for powering a hearing aid 10 and for turning the hearing aid "on" and "off". In this embodiment, a rotary switch member 166 is preferably formed from an insulative material, such as plastic, and covers the respective holes 146 of batteries 142, 143, and 144. It is understood that more than three batteries can be used in accordance with the present invention. Switch member 166 also includes an electrical contact 168, which completes the circuit to power the hearing aid 10 when positioned over a battery, for example, battery 142. Switch member 166 further includes an orifice 170 which provides air to the selected battery to activate the same.

The switch member 166, in one embodiment, is rotated to select and activate a battery by an actuator member 172. In one embodiment, the actuator member 172 is rotatably supported by the housing or shell 74 of the hearing aid 10 and rotates the switch member 166 upon rotation of the member 172 by the user. Preferably, the switch member 166 includes detents thereon to allow the switch member to "click" into position. It the embodiment of FIG. 25, four detents are used—one detent for each battery 142, 143, 144 and one detent for the "off" position. In an alternative embodiment, the actuator member 172 can rotate a member (not shown) which supports the batteries while the switch member 166 remains in place.

Typical hearing instruments are designed to have a product life of approximately 4 to 5 years. As such, the materials selected for these instruments must be robust enough to withstand the normal wear that a given unit will experience during its life-cycle. Since the hearing aids performance and appearance should not degrade significantly within this 4 to 5 year period, this generally means that the materials utilized are relatively hard, contributing to the discomfort experienced by the wear of the instrument.

To address the issue of discomfort, the tip 94 is preferably constructed of a soft, compliant material the shells 74 are formed from a stiff plastic material. It has been found that such a tip construction can dramatically improve the perceived comfort of a unit. However, since the useful life of this highly compliant material is anticipated to be greatly reduced when compared to its relatively stiff counterpart, i.e., shells 74, it may be necessary to intentionally limit the life of the product, so that the user is not put at risk due to the wear degradation of the hearing instrument. Also, since the hearing aid 10 preferably incorporates a zinc-air battery, limiting the product life also minimizes the problems associated with battery swelling due to extreme discharging. Accordingly, three methods for automatic shutdown of a hearing aid are described below.

Figure 26:
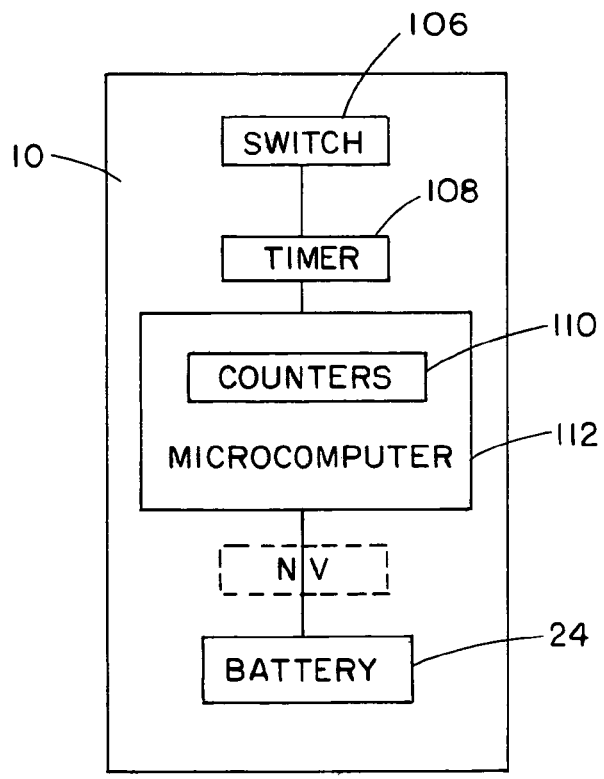
FIG. 26 is a partial schematic of a hearing aid in accordance with the present invention.

A first method monitors the on-time of the hearing aid 10 to determine an appropriate turn-off time. Monitoring can be implemented in software, hardware, or combination of the two. In one embodiment, with reference to FIG. 26, when the hearing aid 10 is turned "on" by switch 106, an electronic timer 108 is started to help keep track of the elapsed time. The output of timer 108 increments counters 110 in a microcomputer 112 in the hearing aid 10 that stores the elapsed time data. So that this data will not be lost when the switch 106 is in the "off" position, power is provided to the counters at all times. Consequently, to avoid excessive battery drain, the power requirements of the counter are preferably minimal. As an alternative to constantly supplying power to the counters, nonvolatile (NV) memory NV can be used to store the on-time data. Although the NV memory will eliminate the need to provide power to the circuitry when the hearing aid is "off", the tradeoff is that there is a power drain associated with storing the information in memory.

When the user moves the switch 106 to the "off" position, the timer 108 is halted. This prevents any increment to the counters 110 while the hearing aid 10 is "off". The on/off cycle described herein repeats until some predetermined time limit is exceeded. Once the time limit is exceeded, the hearing aid 10 is shut down. For example, this can be achieved by disabling the output which drives the receiver 22. However, prior to shutting down the unit, periodic audible warnings of impending shut down can be generated to alert the user of the impending shut down.

A second method tracks the time elapsed from the moment that the user moves the switch 106 to the "on" position. Once again, when the hearing aid 10 is turned "on" by a user, the timer 108 is started. However, in this embodiment, a flag is set in the microcomputer 112 which indicates that the unit has been turned "on" at least one time. The current state of this flag prevents the timer 108 from being shut down when the unit is turned "off". Thus, this timer 108 output continuously increments the counters whether the unit is "on" or "off". After initial actuation of the switch to the "off" position, power is provided to the timer and the counters at all times. This process continues until some predetermined time limit is exceeded. Within the context of a disposable hearing aid, the time limit could correspond to a predetermined number of days, for example, 7, 14 or even 30 days. If the unit is rechargeable, that time limit could be for an extended period of time, for example, 90 days or more. These type of time intervals are preferably relatively easy for the user to remember. Preferably, when the time limit is exceeded, the unit will be shut down after periodic audible warnings of shut down have been generated.

Another shut down method in accordance with the present invention is based on the calendar. In accordance with this embodiment, the hearing aid 10 only operates during a selected month, for example, January only. Since the hearing aid 10 functions only during the selected month, the user benefits by knowing that they should get a replacement unit at (or around) the beginning of each month.

Preferably, this technique is independent of the position of the switch 106 and is implemented in the following manner. First, the hearing aid electronics include a means for tracking date and time. This can be done by supplying date and time information to the circuitry during programming of the hearing aid 10. Since the hearing aid 10 keeps track of the date from this point forward, power is supplied to this watch function. The month over which the hearing aid 10 will operate can be determined when the user first turns "on" the unit for a predetermined time period. This time period in question should be long enough so that inadvertent month selection is avoided. In a preferred embodiment, there is a limit to the number of times that a user may actuate the switch 106 before the hearing aid finally selects the operating month. If desired, the hearing aid 10 may be designed such that it will accommodate a grace period. For example, it can function over a time period that includes the two days before the selected months as well as two days after.

While this invention has been particularly shown and described with references to preferred embodiments thereof, it will be understood by those skilled in the art that various changes in form and details may be made therein without departing from the scope of the invention encompassed by the appended claims.

What is claimed is:

1. A disposable hearing aid having an integrated metal-air battery, the disposable hearing aid enclosed in one of a gas-impermeable and substantially gas-impermeable package, where the package is sealed and maintained at a relative humidity of between 40% and 60% to optimize life of the metal-air battery of the disposable hearing aid.

2. The hearing aid of claim 1, wherein the package is at least partially filled with an inert gas.

3. The hearing aid of claim 2, wherein the inert gas is nitrogen.

4. The hearing aid of claim 1, wherein the relative humidity is maintained in the package at about 50%.

5. The hearing aid of claim 1, wherein the package is gas-impermeable or substantially gas-impermeable to at least one of oxygen, carbon dioxide, and water vapor.

6. The hearing aid of claim 1, wherein the hearing aid is insertable into an ear canal.

7. The hearing aid of claim 1, wherein the hearing aid includes a switch that shuts the hearing aid off in a first position and turns the hearing aid on in a second position.

8. The hearing aid of claim 1, wherein the metal-air battery comprises a zinc-air battery.

9. A method of storing a disposable hearing aid having an integrated metal-air battery, the method comprising sealing the disposable hearing aid in a package that is one of a gas-impermeable and substantially gas-impermeable package at a relative humidity maintained between 40% and 60% to optimize life of the metal-air battery of the disposable hearing aid.

10. The method of claim 9, wherein the package is at least partially filled with an inert gas.

11. The method of claim 10, wherein the inert gas is nitrogen.

12. The method of claim 9, wherein the relative humidity is maintained in the package at about 50%.

13. The method of claim 9, wherein the package is gas-impermeable or substantially gas-impermeable to at least one of oxygen, carbon dioxide, and water vapor.

14. The method of claim 9, wherein the metal-air battery comprises a zinc-air battery.

15. A method of prolonging a storage life of a disposable hearing aid having an integrated metal-air battery, the method comprising encasing the disposable hearing aid in a package that is one of devoid and substantially devoid of detrimental gases at a maintained relative humidity of between 40% and 60% to optimize life of the metal-air battery of the disposable hearing aid.

16. The method of claim 15, wherein at least of one of the detrimental gases includes oxygen.

17. The method of claim 15, wherein at least one of the detrimental gases includes carbon dioxide.

18. The method of claim 15, wherein the package is at least partially filled with an inert gas.

19. The method of claim 18, wherein the inert gas is nitrogen.

20. The method of claim 15, wherein relative humidity is maintained in the package at about 50%.

21. The method of claim 15, wherein the package is gas-impermeable or substantially gas-impermeable.

22. The method of claim 15, wherein the metal-air battery comprises a zinc-air battery.

* * * * *